US 7,976,600 B1

(12) United States Patent
Safuto

(10) Patent No.: US 7,976,600 B1
(45) Date of Patent: *Jul. 12, 2011

(54) DEVICE AND METHOD FOR CONTAINMENT AND ELIMINATION OF TOXIC OR OTHER CONTAMINANT AEROSOLS

(76) Inventor: Joseph Safuto, Glendale, CA (US)

( * ) Notice: Subject to any disclaimer, the term of this patent is extended or adjusted under 35 U.S.C. 154(b) by 232 days.

This patent is subject to a terminal disclaimer.

(21) Appl. No.: 12/317,412

(22) Filed: Dec. 23, 2008

Related U.S. Application Data

(63) Continuation-in-part of application No. 11/106,885, filed on Apr. 15, 2005, now Pat. No. 7,485,166.

(60) Provisional application No. 60/563,203, filed on Apr. 17, 2004.

(51) Int. Cl.
*B01D 46/00* (2006.01)
*B01D 50/00* (2006.01)

(52) U.S. Cl. ............ 55/385.1; 55/385.4; 95/273; 4/300; 4/301; 4/234; 4/235; 4/367.1; 4/371; 4/222; 4/213; 4/217; 220/200; 220/203.22; 220/212; 220/212.5; 220/371

(58) Field of Classification Search ................. 55/385.1, 55/385.4; 95/273; 4/300, 301, 234, 235, 4/367.1, 371, 222, 213–217; 220/200, 371, 220/203.22, 212, 212.5
See application file for complete search history.

(56) References Cited

U.S. PATENT DOCUMENTS

| | | |
|---|---|---|
| 2,849,727 A | 9/1958 | Bollinger et al. |
| 3,365,063 A | 1/1968 | Cobb et al. |
| 3,579,663 A | 5/1971 | Ware et al. |
| 3,689,944 A | 9/1972 | Clayton |
| 4,301,555 A | 11/1981 | Poister |
| 4,344,194 A | 8/1982 | Pearson |
| 4,586,201 A | 5/1986 | Todd, Jr. |
| 4,843,656 A | 7/1989 | Forman |
| 5,079,783 A | 1/1992 | Haletsky et al. |
| 5,426,793 A | 6/1995 | Mac |
| 5,429,240 A | 7/1995 | Biebel et al. |
| 5,539,937 A | 7/1996 | Barefoot |
| 5,864,892 A | 2/1999 | Cool |
| 6,226,807 B1 | 5/2001 | Rozenblatt et al. |

(Continued)

OTHER PUBLICATIONS

U.S. Environmental Protection Agency, Indoor Air—Publications, "Biological Pollutants in Your Home," by Consumer Product Safety Commission (CPSC) and the American Lung Association. The Christmas Seal People; IAQ Publications, www.epa.gov., Oct. 2003.

(Continued)

*Primary Examiner* — Duane Smith
*Assistant Examiner* — Minh-Chau Pham
(74) *Attorney, Agent, or Firm* — Patent Law Agency, LLC; Peter Ganjian

(57) ABSTRACT

A device for detection, collection, containment, neutralization, and elimination of aerosolized contaminants has a lid that fully covers an edge of a toilet bowl for containment of exiting aerosolized contaminants. The lid including a main lid section and a single piece lid cap, with the single piece lid cap having a housing for accommodating an article. The single piece lid cap having a first vent located normal to a natural vertical upward move of the aerosolized contaminants, and a second vent at a back end of the single piece lid cap, oriented substantially parallel to the vertical upward movement of the aerosolized contaminants. The aerosolized contaminants are detected, collected, contained, neutralized, and eliminated by the article within the housing, allowing only uncontaminated air out of the second vent through a natural upward movement of the aerosolized contaminants.

3 Claims, 20 Drawing Sheets

U.S. PATENT DOCUMENTS

| | | | |
|---|---|---|---|
| 6,546,567 | B2 | 4/2003 | Kuzniar |
| 6,895,604 | B1 | 5/2005 | Ramsey |
| 7,485,166 | B2 * | 2/2009 | Safuto .................... 55/385.1 |
| 2004/0019960 | A1 | 2/2004 | Kuzniar |

OTHER PUBLICATIONS

The CLE@NZINE Your Industry News—First. Do your toilets make you sick? The sneeze effect. SneezeEffect.html; www.thecleanzine.com/pages/sneezeeffect.html., Dec. 11, 2003.

Panasonic, "Matsushita (Panasonic) Develops New Air Filter Capable of Inactivating Various Allergens and SARS Virus," Jul. 9, 2004, 2004, http://www.panasonic.co.jp/global/top.html.

Applied Microbiology (American Society of Microbiology), vol. 30, No. 2, Aug. 1975, p. 229-237, titled "Microbiological Hazards of Household Toilets: Droplet Production and the Fate of Residual Organisms," by Charles P. Gerba et.

Consensus Statement by the World Health Organization (WHO) in Rome, Sep. 23-25, 2003. Titled "WHO Informal Consultation on the Transmission of SARS CoV and Other Pathogenic Viruses Through Fecal Droplets."

The New England Journal of Medicine, published Apr. 22, 2004, vol. 350:1731-1739, No. 17, titled "Evidence of Airborne Transmission of the Severe Acute Respiratory Syndrome Virus."

* cited by examiner

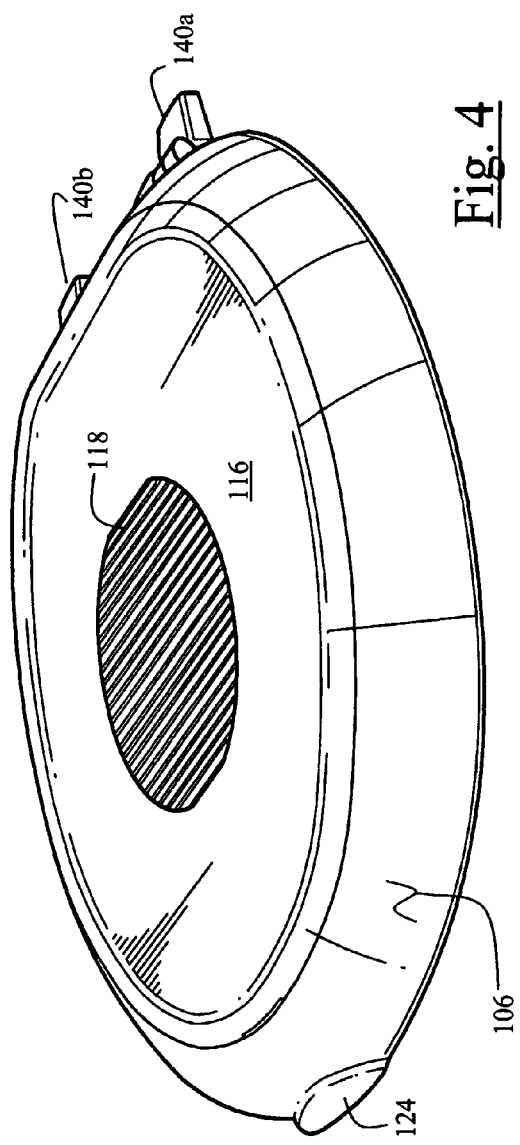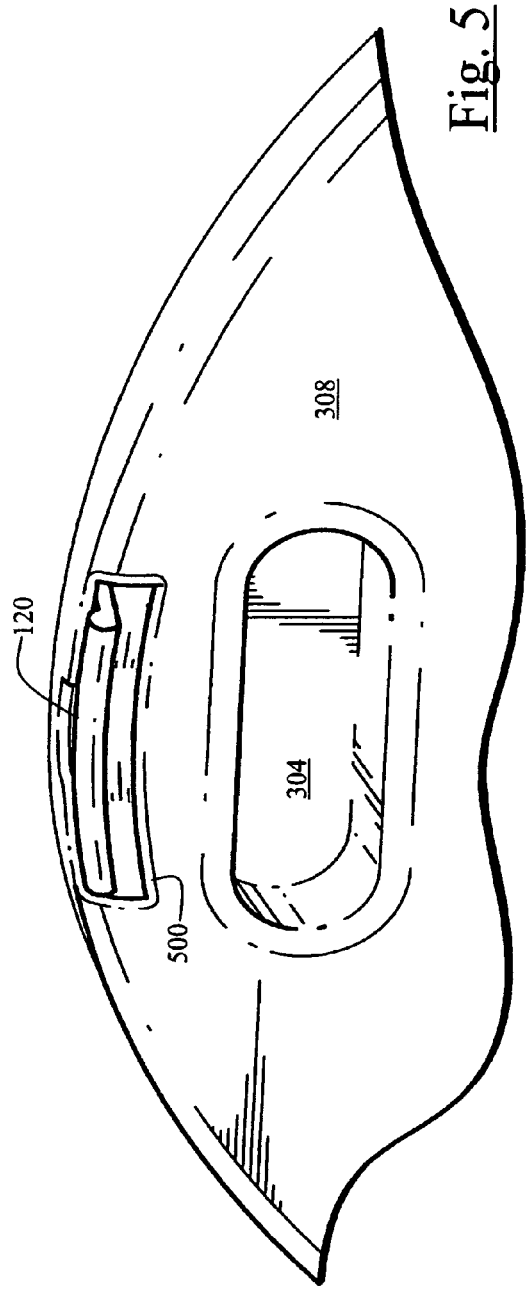

US 7,976,600 B1

DEVICE AND METHOD FOR CONTAINMENT AND ELIMINATION OF TOXIC OR OTHER CONTAMINANT AEROSOLS

CROSS-REFERENCE TO RELATED APPLICATIONS

This application is a Continuation-In-Part application claiming the benefit of priority of the prior co-pending U.S. Utility Non-Provisional patent application Ser. No. 11/106,885, with a filing date of Apr. 15, 2005, now U.S. Pat. No. 7,485,166 B2, which application (Ser. No. 11/106,885) claims the benefit of priority of U.S. Utility Provisional Patent Application Ser. No. U.S. 60/563,203, filed Apr. 17, 2004, the entire disclosures of all applications are expressly incorporated by reference in their entirety herein.

BACKGROUND OF THE INVENTION

1. Field of the Invention

This invention relates in general to lids and pertains, more particularly, to toilet lids for containment and elimination of aerosolized contaminants such as fecal and urinary matter, and various airborne toxic, virus and bacterial mist.

2. Description of Related Art

Based on extensive research, it has been proven that after each toilet flush an airborne bacterial and viral plume permeates the entire bathroom or water closet area leaving a residue on anything within the "flush zone." Whether the toilet lid is closed or open, after every flush fecal, urine, and toxic aerosol (droplets in mist form) can spew up to about 20 feet away (also known as the "sneeze effect"), landing on any item within range.

A study published in Applied Microbiology (American Society of Microbiology), Vol. 30, No. 2, August 1975, p. 229-237, titled "Microbiological Hazards of Household Toilets: Droplet Production and the Fate of Residual Organisms," by Charles P. Gerba et al. disclosed the extensive transmission of viral aerosols from toilets. The study conducted in 1975 found that "bacteria and viruses in household toilets were shown to remain in the bowl after flushing, and even continual flushing could not remove a persistent fraction. The study further stated that "The detection of bacteria and viruses falling out onto surfaces in bathrooms after flushing indicated that they remain airborne long enough to settle on surfaces throughout the bathroom." The Gerba et al. study stated that "Thus there is a possibility that a person may acquire an infection from an aerosol produced by a toilet."

The Consensus Statement by the World Health Organization (WHO) in Rome, Sep. 23-25, 2003, Titled "WHO Informal Consultation On The Transmission Of SARS CoV And Other Pathogenic Viruses Through Fecal Droplets," hereinafter "WHO," discussed the "risks of transmission of SARS CoV amongst human population associated with the design and operation of sanitation facilities for the management of human excreta." More recently, concerning the WHO findings, The New England Journal of Medicine, published Apr. 22, 2004, Volume 350:1731-1739, Number 17, titled "Evidence of Airborne Transmission of the Severe Acute Respiratory Syndrome Virus," (or SARS) suggested a clear connection between the SARS virus and aerosolized fecal matter airborne through the simple act of flushing a toilet.

A plethora of conventional toilet lid devices integral with electro-mechanical air deodorizing devices for deodorizing the air from a toilet bowl are disclosed in the prior art. Reference is made to U.S. Pat. Nos. 6,895,604; 6,546,567; 6,226,807; 5,539,937; 5,429,240; 5,426,793; 5,079,783; 4,843,656; 4,586,20; 4,344,194; 4,301,555; 3,689,944; 3,579,663; 3,365,063; and 2,849,727; and U.S. Patent Application Publications 2004/0019960. Most use complicated electrical/mechanical venting systems that include the use of electrical exhaust fans and air duct connected with the fans to electromechanically vent and remove odors from the toilet bowls, with others claiming the removal (or vacuuming) of odors and germs. Regrettably, according to WHO, it has been found that the use of mechanical or electrical devices as a venting system may exacerbate the spread of toxins, viruses, and bacteria rather than eliminate them. In fact, the recommendation of WHO was that "Whenever possible, venting systems should be free of mechanical devices." One reason for this is that air conduits or pipes, fans, etc. that are used in the prior art devices can easily become clogged with fecal, urine, and mildew, which can increase the spread of bacteria and viruses. In addition, most prior art devices disclosed require expensive structural modifications to the bathroom and the toilet seat and lid (addition of holes in the walls of the water closets to run the air pipes, place fans, etc.). They also require power to operate, which requires additional outlets or storage areas for batteries, requiring further structural modifications of the bathrooms, water closets, and toilets. Furthermore, all the additional mechanical features also require constant maintenance, which is an added cost to consumers.

The U.S. Pat. No. 5,864,892 to Cool disclosed a device and method for collecting and sanitizing toilet spray without the use of mechanical devices by placing a cover over a conventional toilet, including the toilet lid, seat, and bowl. However, with the Cool device, any liquid that drips along the exterior of the toilet bowl or on the underside of the toilet seat and does not contact the cover is not sanitized, and remains a potential agent for transmission of bacteria and viruses. Therefore, when the cover is removed for maintenance, the fecal and urinary residue in contact with the toilet bowl or seat can contaminate the person cleaning it, and cause the bacteria and viruses to become airborne again. In addition, the cover is not esthetically pleasing and alters the conventional manner in which toilets are generally used.

To date, no provision is made to ensure that the water splash and mist created during toilet flushing is collected, contained, neutralized, and eliminated within the toilet bowl. No prior art has provided a toilet lid for collection and containment of aerosolized toxic contaminants or fecal and urinary matter, including various airborne viruses and bacterial mist without the use of mechanical or electrical devices, modification of the toilet bowl or water closet, or addition of accessories such as toilet covers.

In light of the current state of the art and the drawbacks to current devices and methods mentioned above, a need exists for a toilet lid that would permit for collection, containment, and elimination of aerosolized contaminates such as toxins, or fecal and urinary matter including various airborne viruses and bacterial mist within the toilet bowl, without the use of mechanical or electrical systems, accessory covers, and modification of the toilet bowl or the water closet.

BRIEF SUMMARY OF THE INVENTION

The present invention provides a non-mechanical, non-electrical, non-moving toilet seat and lid combination for containment and elimination of aerosolized contaminants such as fecal and urinary matter, and various airborne toxins, viral, and bacterial mist, and works with the natural fluid dynamics caused by flushing a toilet that generates the vertical ascension of aerosols via the force of the conventional flush.

One aspect of the present invention provides a device for containment and elimination of aerosolized contaminants, comprising:
- a toilet lid coupled with a toil seat, and when in a closed position, a first gap between the toilet lid and the toilet seat is fully enclosed to contain and block exiting aerosolized contaminants through the first gap during a flush;
- the toilet seat is comprised of a continuous seal coupled with an underside of the toilet seat to fully enclose a second gap between the toilet seat and a top surface opening of a toilet bowl when the toilet seat is in the closed position to contain and block exiting aerosolized contaminants through the second gap during the flush;
- the toilet lid including a main lid section and a single piece lid cap that is detachably coupled with the main lid section;
- the single piece lid cap includes a placement for accommodating an article, and further includes a first vent and a second vent, with the article positioned within the placement, in between the first and the second vents;
- the placement includes a retainer lip to securely, and removably retain the article on top of the first vent;
- with the toilet lid and the toilet seat in closed positions to close the first and the second gaps, when water is delivered into the toilet bowl, the delivered water displaces and compresses air within the toilet bowl, generating an increasing air pressure therein that is pushed upward as a volume of delivered water continues to increase and fill the toilet bowl, with the increased volume of water pushing the pressurized air and the aerosolized contaminants within the toilet bowl vertically up to ascend and exit the toilet bowl through the first vent, the article, and then the second vent at the back end of the single piece lid cap, while the closed first and the second gaps block exiting of the aerosolized contaminants;
- the first vent is located normal to the vertical upward move of the aerosolized contaminants, and the second vent is located at a back end of the single piece lid cap, oriented substantially parallel to the vertical upward move of the aerosolized contaminants;
- with the aerosolized contaminants detected, collected, contained, neutralized, and eliminated by the article, allowing only uncontaminated air out of the first and second vents, and only through the natural upward movement of the aerosolized contaminants due to the flush cycle, without using electrical or moving components.

An exemplary, optional aspect of the present invention provides a device for containment and elimination of aerosolized contaminants, wherein:
- the main lid section further including a top surface that is smooth; and
- a shroud section that fully covers and extends past a bottom edge of the toilet bowl for covering gaps between the lid and the toilet bowl for containment of exiting aerosolized contaminants.

Another exemplary, optional aspect of the present invention provides a device for containment and elimination of aerosolized contaminants, wherein:
- an underside of the single piece lid cap is contoured to rest and be commensurately congruent with a top surface of the toilet seat, forming a tight, snug fit seal; and
- the underside of the single piece lid cap further includes a substantially protruded section, which, when in closed position in relation to the toilet seat, is moved into a correspondingly configured toilet seat opening, with the protruded section having an elevation that is inversely contoured to complement an inner edge periphery of the toilet seat, further facilitating a tight seal between the toilet lid and the toilet seat.

These and other features, aspects, and advantages of the invention will be apparent to those skilled in the art from the following detailed description of preferred non-limiting exemplary embodiments, taken together with the drawings and the claims that follow.

BRIEF DESCRIPTION OF THE DRAWINGS

It is to be understood that the drawings are to be used for the purposes of exemplary illustration only and not as a definition of the limits of the invention. Throughout the disclosure, the word "exemplary" is used exclusively to mean "serving as an example, instance, or illustration." Any embodiment described as "exemplary" is not necessarily to be construed as preferred or advantageous over other embodiments.

Referring to the drawings in which like reference character (s) present corresponding part(s) throughout:

FIG. 4 is a perspective exemplary illustration of an assembled toilet seat and lid in the closed position in accordance with the present invention;

FIG. 5 is a perspective exemplary view of a locking clip and grip in accordance with the present invention;

DETAILED DESCRIPTION OF THE INVENTION

Figure 1:
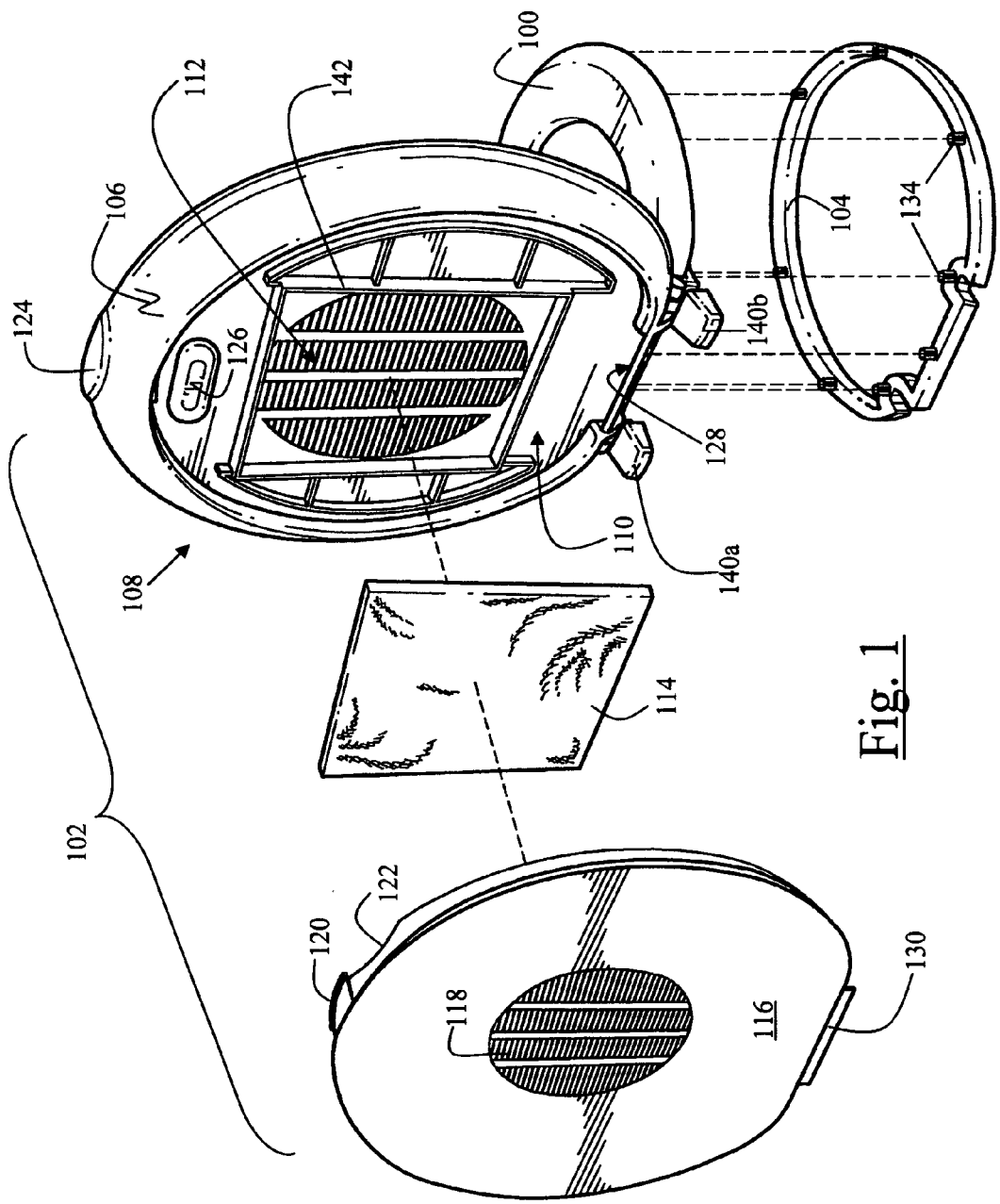
FIG. 1 illustrates a general exemplary toilet seat and lid combination in accordance with the present invention.

Most conventional toilet lids or seats use complicated mechanical and or electrical contraptions to vacuum out odors or germs from toilet bowls from the sides of the toilet seats or bowls. The toilet seats or bowls are equipped with side-vents on the circumference or periphery of bowls or seats that are connected to an electrical fan with a vent pipe that connects to an air duct with another electrical exhaust fan for removal of odors and germs from the building. Although the act of flushing spews out most of the fecal and urinary droplets from the toilet bowl (the "sneeze effect") vertically upward, the mechanical/electrical devices vacuum the odor and germs horizontally through the sides of the toilet, making the complicated contraptions virtually ineffective.

The present invention provides a non-mechanical/electrical toilet seat and lid combination for containment and elimination of aerosolized contaminants such as fecal and urinary matter, various airborne toxins, viral, and bacterial mist, and works with the natural fluid dynamics caused by flushing a toilet that generates the vertical ascension of aerosols. During every flush cycle, a vertically ascending aerosol (spray) is created when the water is pushed in the bowl, and suction is created within the bowl when the water leaves the bowl, pulling the air into the bowl. The flush cycle of a toilet is very well known, and in most cases includes generating a siphon effect, removing water from bowl, and refilling the bowl with water. The present invention very effectively uses this well known flush cycle to contain and eliminate aerosolized contaminants without the use of any electrical/mechanical parts, UV systems, or moving parts, such as fans, motors, vacuum tubes, or any other device not part of a conventional toilet, but uses only the natural, well-known function of a flush.

In general, during a first phase of a typical conventional flush cycle, water is delivered into the toilet bowl to effect a siphon. The delivered water displaces and compresses air within the toilet bowl. This generates an increasing air pressure therein that is pushed upward and laterally as the delivered water continues to fill the toilet bowl rapidly to effect a siphon. The pressurized air (moving upward or laterally) takes the path of least resistance, pushing along with it the aerosolized contaminants within the toilet bowl, vertically up to ascend and to exit the toilet bowl.

During a second phase of a typical conventional flush cycle, water leaves the toilet bowl as a result of the siphon and a natural gravitational pull, generating a suction that pulls in air into the toilet bowl. Finally, during a third (and final) phase of a typical conventional flush cycle, the toilet bowl is refilled with water, which displaces and compresses air within the toilet bowl. This also generates an increasing air pressure therein that is pushed upward as the delivered water continues to fill the toilet bowl. The delivered water pushes the pressurized air and the remaining aerosolized contaminants within the toilet bowl vertically up to ascend and exit the toilet bowl.

The present invention effectively and efficiently uses the above conventional flush cycle of a conventional toilet to detect, collect, contain, and sanitize most of the aerosolized contaminants such as fecal and urinary matter, various airborne toxins, viral, and bacterial mist as a result of the vertical ascension of aerosols after every flush, and closes any gaps between the toilet lid and seat, and seals the toilet seat and bowl for any possible horizontal (lateral) travel of the aerosol caused by the normal conventional flushing, but without the use of an electrical/mechanical devices.

The present invention provides a device comprising a lid that fully covers edges of a container such as a toilet bowl for containment of exiting aerosolized contaminants. The lid includes housing for accommodating an article, non-limiting examples of which may include any one or combination of well-known sensors, analyzers, collectors, filters, sanitizers, etc. The housing includes one or more vents, with one vent optionally smaller in size than the other vent, with the housing and at least one of the vents optionally located normal to a natural vertical upward move of the aerosolized contaminants due to the force of the flush. When the lid of the present invention is in the closed position, the lid and the article within the lid housing can be used to detect, collect, contain, neutralize, and eliminate contaminants that ascend through the top of the container, without the use of any electrical/mechanical or moving parts. In case of a toilet bowl, the contaminants are aerosolized and spewed vertically upward by the normal action of flushing. Hence, the present invention uses the natural fluid dynamics caused by flushing a toilet (and not mechanical/electrical systems) to detect, collect, contain, neutralize, and eliminate most of the aerosolized contaminants, fecal and urinary matter, and various airborne toxins, viral, and bacterial mist as a result of the vertical ascension of aerosols or vapors.

The present invention provides a toilet lid coupled with a toil seat, and when the toilet lid is in a closed position, an entire underside of the toilet lid directly and physically contacts and rests on a top surface of the toilet seat. The toilet lid further including a shroud section that fully covers and extends past an exterior facing edge of the toilet seat and a top surface opening of a toilet bowl when the toilet lid is in the closed position, with the shroud directly and physically contacting an entire exterior facing edge of the toilet seat. The underside of the toilet lid and the shroud fully enclose a first gap between the toilet lid and the toilet seat when the toilet lid is in the closed position, containing exiting aerosolized contaminants and blocking exiting of aerosolized contaminants through the first gap during a flush. The toilet seat of the present invention is further comprised of a continuous seal coupled with an underside of the toilet seat to fully enclose a second gap between the toilet seat and the top surface opening of the toilet bowl when the toilet seat is in the closed position, containing exiting aerosolized contaminants and blocking exiting of aerosolized contaminants through the second gap during the flush. The toilet lid further has a housing for accommodating an article, with the housing comprising one or more vents. When the toilet lid and the toilet seat are in closed positions to close the first and the second gaps, when flushing, water is delivered into the toilet bowl to effect a siphon, the delivered water displaces and compresses air within the toilet bowl, generating an increasing air pressure therein that is pushed upward as a volume of delivered water continues to increase and fill the toilet bowl. With the increased volume of water pushing and further pressurizing air therein, the aerosolized contaminants within the toilet bowl move vertically up to ascend and exit the toilet bowl through the vents provided by the present invention, while the closed first and the second gaps block exiting of the aerosolized contaminants, which are detected, collected, contained, neutralized, and eliminated by the article within the housing. This allows only uncontaminated air out of the vent, and only through a natural upward movement of the aerosolized contaminants due to the flush cycle, without using electrical/mechanical or moving components.

Referring to FIGS. 1 to 16F and, FIG. 1 in particular, the lid 102 of one embodiment of the present invention is comprised of a main lid section 108 having a shroud 106 that fully covers a gap between the lid 102 and a seat 100 by extending past a bottom edge of the toilet seat 100. That is, the shroud section 106 fully covers and extends past an exterior facing edge of the toilet seat 100 and a top surface opening of a toilet bowl 700 (FIG. 7) when the toilet lid 102 is in the closed position, with the shroud 106 directly and physically contacting an entire exterior facing edge of the toilet seat 100. The underside of the toilet lid 102 and the shroud 106 fully enclose a first gap between the toilet lid 102 and the top surface of the toilet seat 100 when the toilet lid 102 is in the closed position, containing exiting aerosolized contaminants and blocking exiting of aerosolized contaminants through the first gap during a flush. In other words, when the lid 102 is in a fully closed position (illustrated in FIG. 4), the entire underside 308 of the toilet lid 102 directly and physically contacts and rests on a top surface of the toilet seat 100, which seal and close the first gap. In addition, the shroud 106 further facilitates in blocking of exiting of fecal and urinary aerosols during the act of flushing. The proximal end of the shroud 106 includes a lid lift tab 124 that facilitates in raising and lowering the lid 102 without touching the seat 100. As illustrated, the lid lift tab 124 is arched, and extends out, past the outer edge of the seat 100 to allow a person to use a finger to lift or lower the lid 102.

Figure 2:
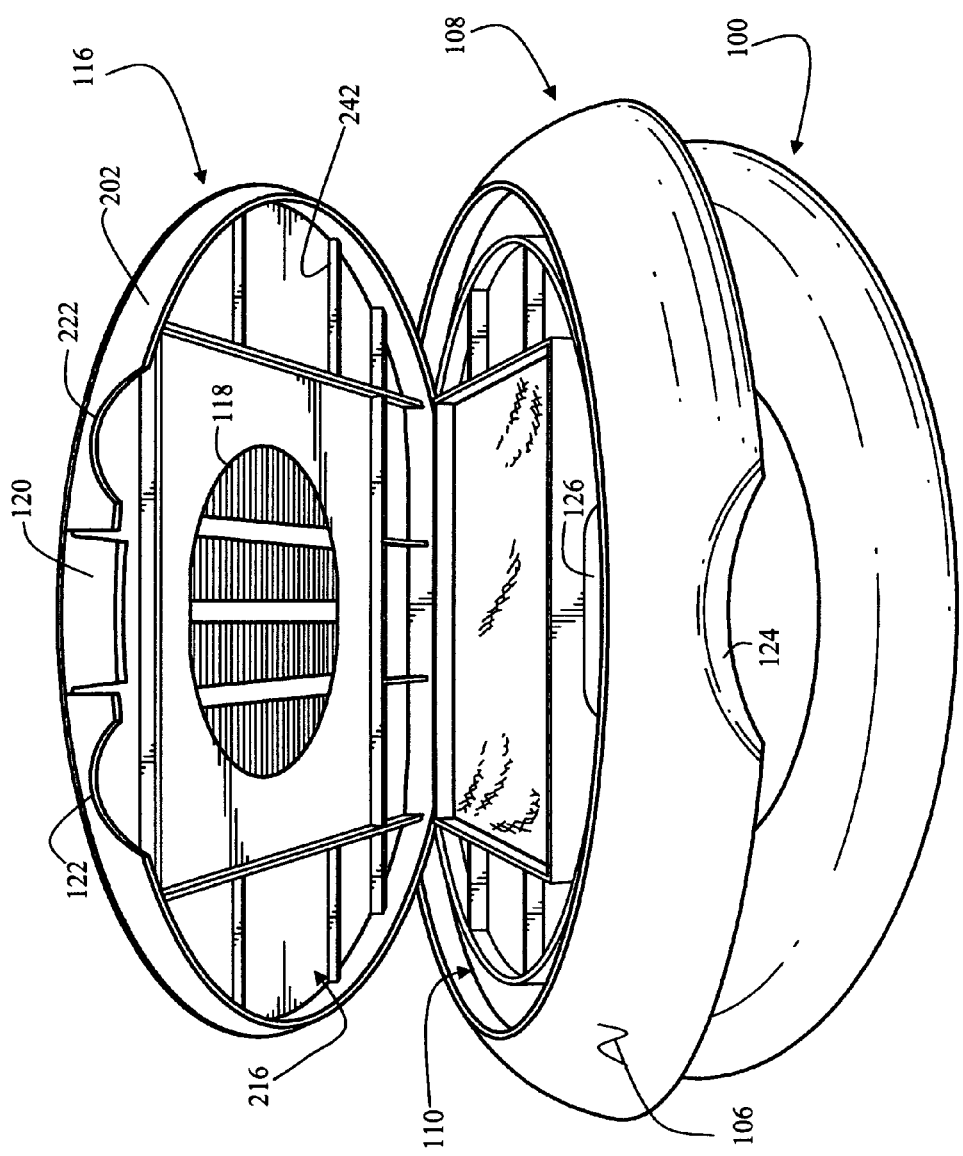
FIG. 2 is a perspective exemplary front illustration of the toilet seat, lid, and lid cap, unassembled, in accordance with the present invention.

As further illustrated in FIG. 1, the main lid section 108 includes a housing 110 comprised of a vent or air holes 112. The housing 110 can be used to store any article 114 of appropriate size, the non-limiting examples of which may include one or any combination of well-known sensors, analyzers, filters, collectors, sanitizers, etc. to detect, collect, contain, neutralize, and or eliminate aerosolized contaminants that ascend vertically out of the toilet bowl as a result of flushing, without any mechanical or electrical devices or moving parts, when the seat 100 and lid 102 are in the closed position. The housing 110 also includes structures 142 for securing the article 114, and for providing structural integrity and strength for the lid 102. The housing 110 further includes an elongated recessed portion 128 at a distal end near the two coupling hinges 140a and 140b for accommodating a protruded tab 130 located at a distal end of a lid cap 116. The coupling hinges 140a and 140b reference a mechanism that couples the entire lid/seat combination to the toilet bowl. In addition, the housing 110 includes an opening 500 at a proximal end thereof (best illustrated in FIG. 5) for receiving a locking clip 120 located at a proximal end of the lid cap 116. As best illustrated in FIGS. 1, 2, and 5, the locking clip 120 is comprised of a cut-section from the circumference edge 202 of the lid cap 116, suspended in a cantilever manner that interlocks within the edges of opening 500 of the housing 110.

The housing 110 is closed by a removable lid cap 116, which also includes a vent or air holes 118 at a location commensurate with a location of the vent or air holes 112 on the main lid section 108. In general, it is preferred (optionally, only) if the size of the vent 118 on the lid cap is optionally made smaller than the size of the vent 112 on the main lid section 108. However, the device of the present invention can function without size differences between the vents. In general, the size difference (smaller top vent and larger bottom vent) accelerates the venting process. That is, this difference may facilitate the acceleration of the vertical ascension of aerosols through the vent 112, the housing 110, pushing air out of the vent 118. As best illustrated in FIGS. 1 and 2, the lid cap 116 includes a right 222 and a left 122 arch located at a proximal end thereof, near both sides of the locking clip 120 for facilitating the removal and insertion of the lid cap 116 from the main lid section 108. As best illustrated in FIGS. 2 and 4, the circumference edge 202 of the lid cap 116 is fully inserted inside the housing 110. The underside 216 of the lid cap 116 also includes support structure 242 for added strength.

Figure 6:
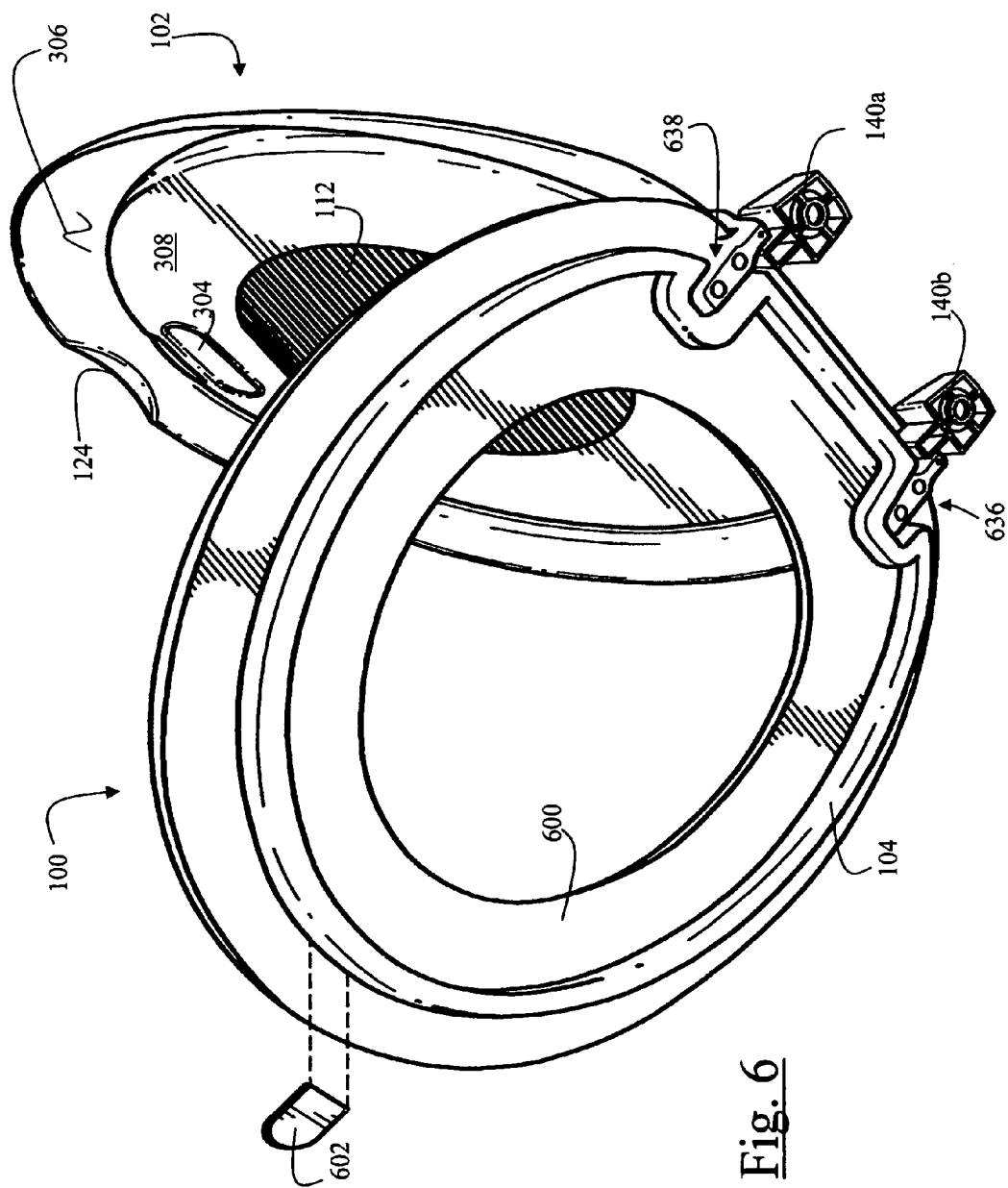
FIG. 6 is a perspective exemplary illustration of the underside of the toilet seat in accordance with the present invention.
Figure 7:
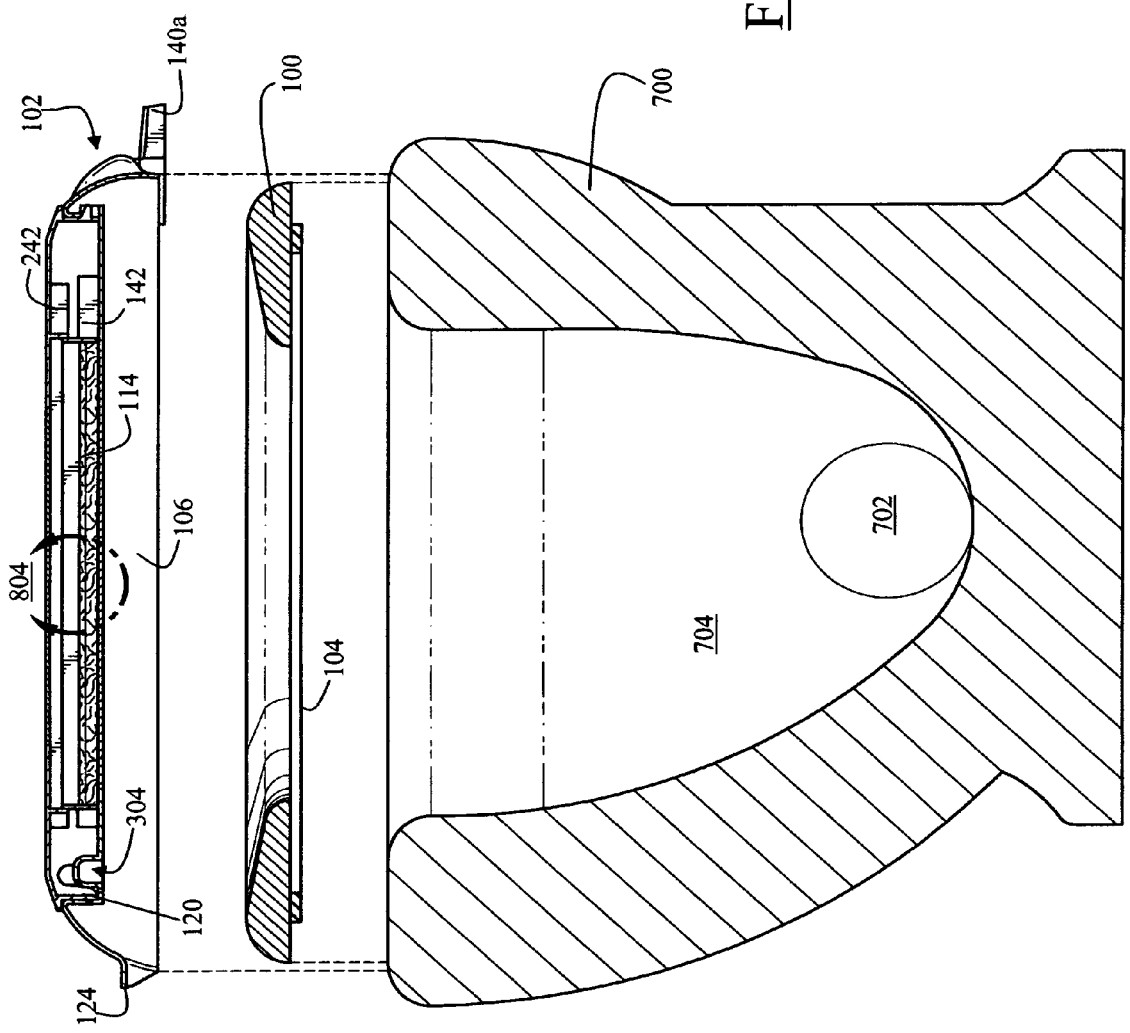
FIG. 7 is a side cross-sectional view, illustrating an exemplary toilet bowl, seat, and lid in accordance with the present invention.

Referring to FIGS. 1, 6, and 7, the seat 100 is comprised of a continuous seal 104 that is connected to the underside 600 of the seat 100 by one or more seal installation tabs 134 to enclose the gap between the toilet seat 100 and a top surface opening of the toilet bowl 700 (FIG. 7) when the toilet seat 100 is in the closed position. This closing of the gap prevents the exiting of any possible horizontally (lateral) moving toxins, fecal, or other contaminant aerosols due to flushing when the lid and seat are in the closed position (illustrated in FIG. 4). The seal installation tabs 134 are inserted into a commensurate number of apertures (not shown) within the underside 600 of the seat 100. As best illustrated in FIG. 6, the seal 104 is continuously placed around the underside 600 of the toilet seat 100, veering around connection mechanisms 636 and 638 at a distal end of the toilet seat 100, near the coupling hinges 140a and 140b. The connection mechanisms 636 and 638 may be used to couple the seat 100 to the lid 102. As further illustrated in FIG. 6, the toilet seat 100 and lid 102 combination of the present invention also includes an optional seat lift tab 602 that facilitates in raising and lowering of the toilet seat 100.

Figure 3:
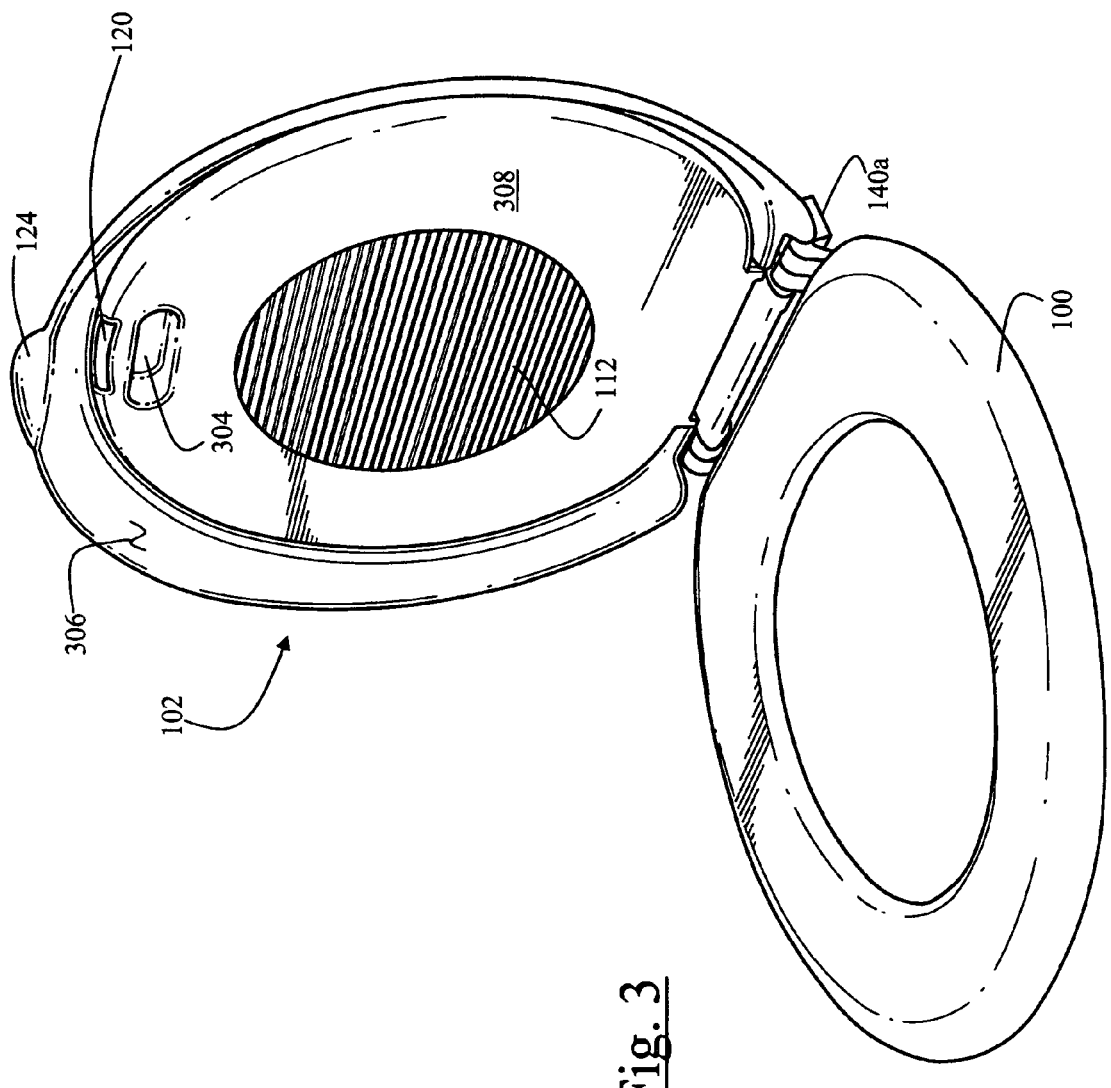
FIG. 3 is a perspective exemplary illustration of an assembled toilet seat and lid in the open position in accordance with the present invention.

FIG. 3 is a perspective exemplary illustration of an assembled toilet seat 100 and lid 102 in the open position in accordance with the present invention, which shows the underside 308 of the main lid section 108 of lid 102. As illustrated, approximately at the middle section of the underside 308 is the underside of the vent 112. The underside 308 further includes a cavity 304 at a proximal end near the opening 500 (best illustrated in FIG. 5) for insertion of fingers for grasping the lid cap for facilitating the removal of the locking clip 120 from the opening 500. The opposite side of the cavity 304 is referred to by the reference number 126 in the FIGS. 1 and 2, and is illustrated as a bump or protuberance. FIG. 3 also illustrates the underside 306 of the shroud 106.

FIG. 4 is a perspective exemplary illustration of the assembled toilet seat 100 and lid 102 combination in the closed position in accordance with the present invention. As illustrated, the lid 102 completely covers the seat 100 by the shroud 106, and further, as illustrated in both FIGS. 3 and 4, unlike the prior art contraptions, the seat 100 and lid 102 combination of the present invention maintain the same esthetic look and feel of a conventional toilet seat and lid. In particular, the circumference edge 202 of the lid cap 116 fully inserts into the housing 110, enabling a top surface of the lid cap 116 to be flush with the main lid section 108.

Figure 8:
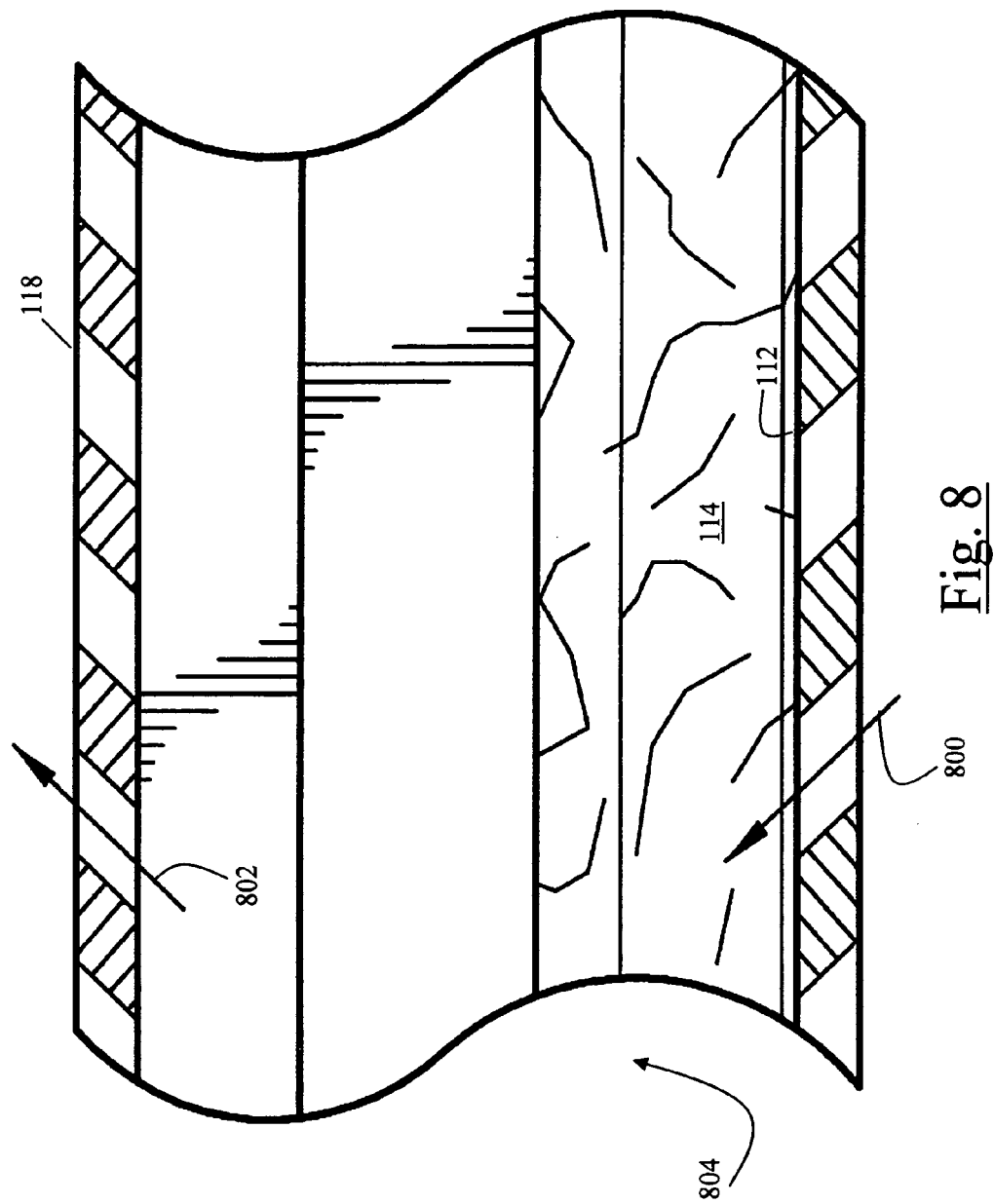
FIG. 8 is an exploded cross-sectional view of an exemplary vent in accordance with the present invention.

FIGS. 7 to 10 illustrate the toilet seat 100 and lid 102 combination of the present invention in relation to the toilet bowl 700. FIG. 7 is a side cross-sectional view, illustrating the cooperative relationship and arrangement of the toilet seat 100, the lid 102, and the toilet bowl 700. The figure also illustrates the toilet water 704 within the bowl 700 and a drainpipe 702. The broken circular arrows 804 in FIG. 7 refer to the drawing illustrated in FIG. 8, which is an enlarged cross-sectional view of the exemplary lid 102 of the present invention, including the article 114 housed within the housing 110. As best illustrated in FIG. 8, during the act of flushing, aerosolized contaminants 800 are spewed vertically up, towards the lid 102, passing through the vent 112 and the article 114 (e.g., a known filter), with clean air 802 coming out of the vent 118 of the lid 116.

Figure 9:
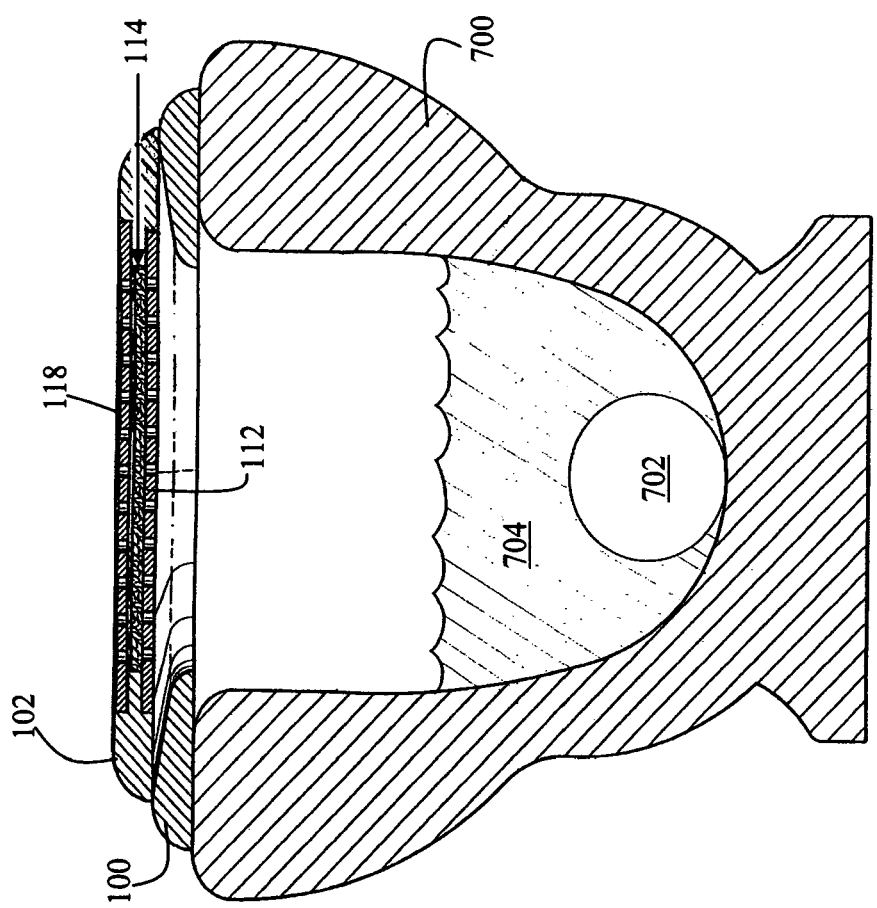
FIG. 9 is a front cross-sectional view, illustrating an exemplary toilet bowl, seat, and lid in accordance with the present invention.
Figure 10:
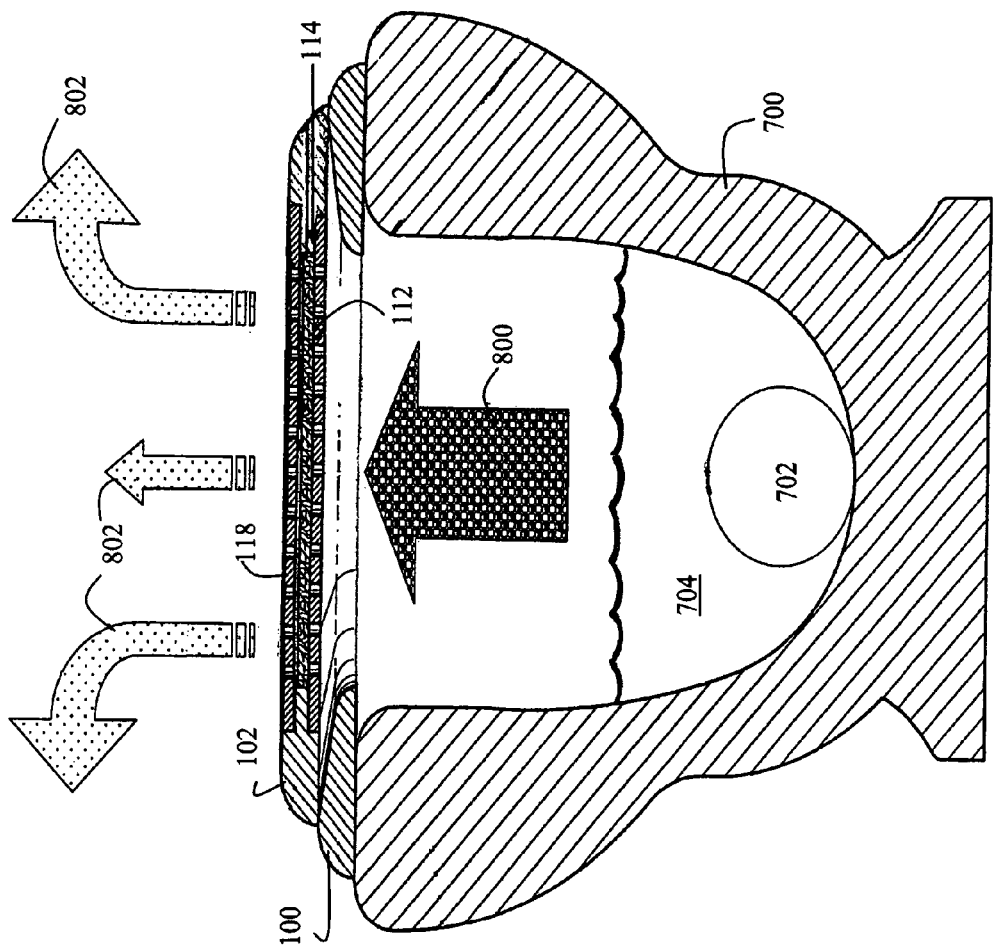
FIG. 10 is a front cross-sectional view, illustrating an exemplary toilet bowl, seat, and lid during flushing action, including the flow dynamics of aerosolized contaminants in accordance with the present invention.

FIG. 9 illustrates a front cross-sectional view, showing a fully assembled and connected toilet bowl 700, seat 100, and lid 102, and FIG. 10 is the same view, illustrating the flushing action, including the flow dynamics of aerosolized contaminants 800 in accordance with the present invention. In both FIGS. 9 and 10, the shroud 106 is not illustrated for clarity. When the seat 100 and the lid 102 are in the closed position, during the first half of the flush cycle (illustrated in FIG. 10), a vertically ascending toxic, bacterial, and viral aerosol (spray) 800 is created (the "sneeze effect") when the toilet water 704 is pushed in the bowl 700. The aerosol or other contaminants (toxins, bacteria, viruses, etc.) 800 is mostly spewed vertically, and is forced to exit through the vent or air holes 112 and the housing 110, but only uncontaminated air 802 is exited through the vent or air holes 118. Upon coming into contact with the article 114 within the housing 110 (which may contain any combination of sensors, analyzers, container dishes, filter-sanitizers, etc.), most of the contaminants or bacteria and viruses are detected, collected, contained and or killed by the article 114, allowing uncontaminated air 802 to exit from the vent 118. During second half of every flush cycle, a suction is created within the bowl 700 when the toilet water 704 leaves the bowl 700 through the drainpipe 702, pulling the air into the bowl 700 through the vent or air holes 118, the housing 110, and the vent or air holes 112. Accordingly, the present invention prevents droplets or airborne toxins, contaminants, or other bacterial or viral aerosols 800 to plume and permeate out of the toilet bowl 700 when the seat 100 and lid 102 combination of the present invention are in the closed position.

More particularly, the present invention closes a first gap or opening between the toilet lid 102 and the toilet seat 100 to contain and block exiting aerosolized contaminants 800 during a flush. The present invention further closes a second gap or opening between the toilet seat 100 and the top surface opening of the toilet bowl 700 when the toilet seat 100 is in the closed position to contain and block exiting aerosolized contaminants during the flush. Enclosing the first and second openings create a single means of escape for air within the toilet bowl, which is only through the disclosed vents. Another purposes for closing the first and the second opening is to generate an air pressure within the toilet bowl when the water is pushed into the commode during the flush to effect a siphon. The pressurized air, due to delivered water into the toilet bowl pushes any aerosolized contaminant out of the bowl through the disclosed vents during the flush cycle without using electrical, UV systems, or any moving parts such as fans, motors, vacuum tubes, and only through the natural, well-known function of a flush.

More technically, the toilet lid 102 and the toilet seat 100 in closed positions, close the first and the second gaps or openings. During a first phase of a flush cycle, water 704 is delivered into the toilet bowl 700 to effect a siphon. The delivered water 704 displaces and compresses air within the toilet bowl. This generates an increasing air pressure therein the bowl (due in part to the sealing or blocking of first and second gaps) that is pushed upward and laterally as a volume of delivered water continues to increase and fill the toilet bowl 700 to effect a siphon. With the increased volume of water pushing the pressurized air, the aerosolized contaminants within the toilet bowl 700 have no other escape but to move vertically up to ascend and exit the toilet bowl through the only openings, which are the disclosed vents, while the closed first and the second gaps block exiting of the aerosolized contaminants. That is, the pressurized air (moving upward or laterally) takes the path of least resistance, pushing along with it the aerosolized contaminants within the toilet bowl 700 vertically up to ascend and to exit the toilet bowl 700 through the vents, while the closed first and the second gaps block exiting of the aerosolized contaminants, without using electrical, UV systems, or any moving parts such as fans, motors, vacuum tubes, and only through the natural, well-known function of a flush.

During a second phase of the flush cycle, water 704 leaves the toilet bowl 700 as a result of the siphon and a natural gravitational pull, generating a suction that pulls in air into the toilet bowl 700 through vents, while the closed first and the second gaps block movement of air through the first and the second gaps. During a third (final) phase of the flush cycle, the toilet bowl is refilled with water 704, which displaces and compresses air within the toilet bowl 700. This generates an increasing air pressure therein that is pushed upward as the delivered water 704 continues to fill the toilet bowl 700. The delivered water pushes the pressurized air and remaining aerosolized contaminants within the toilet bowl 700 vertically up to ascend and exit the toilet bowl through the vents (or openings), while the closed first and the second gaps block exiting of any remaining aerosolized contaminants.

FIGS. 11 to 16F are exemplary illustrations of a various alternative embodiments of toilet lid/seat combinations in accordance with the present invention. The toilet lid/seat combinations illustrated in FIGS. 11 to 16F may include similar corresponding or equivalent components and or interconnections as those shown in FIGS. 1 to 10 and described above. Therefore, for the sake of brevity, clarity, convenience, and to avoid duplication, the general description of FIGS. 11 to 16F may not repeat every corresponding or equivalent component and or interconnections that has already been described above in relation to FIGS. 1 to 10.

Figure 11:
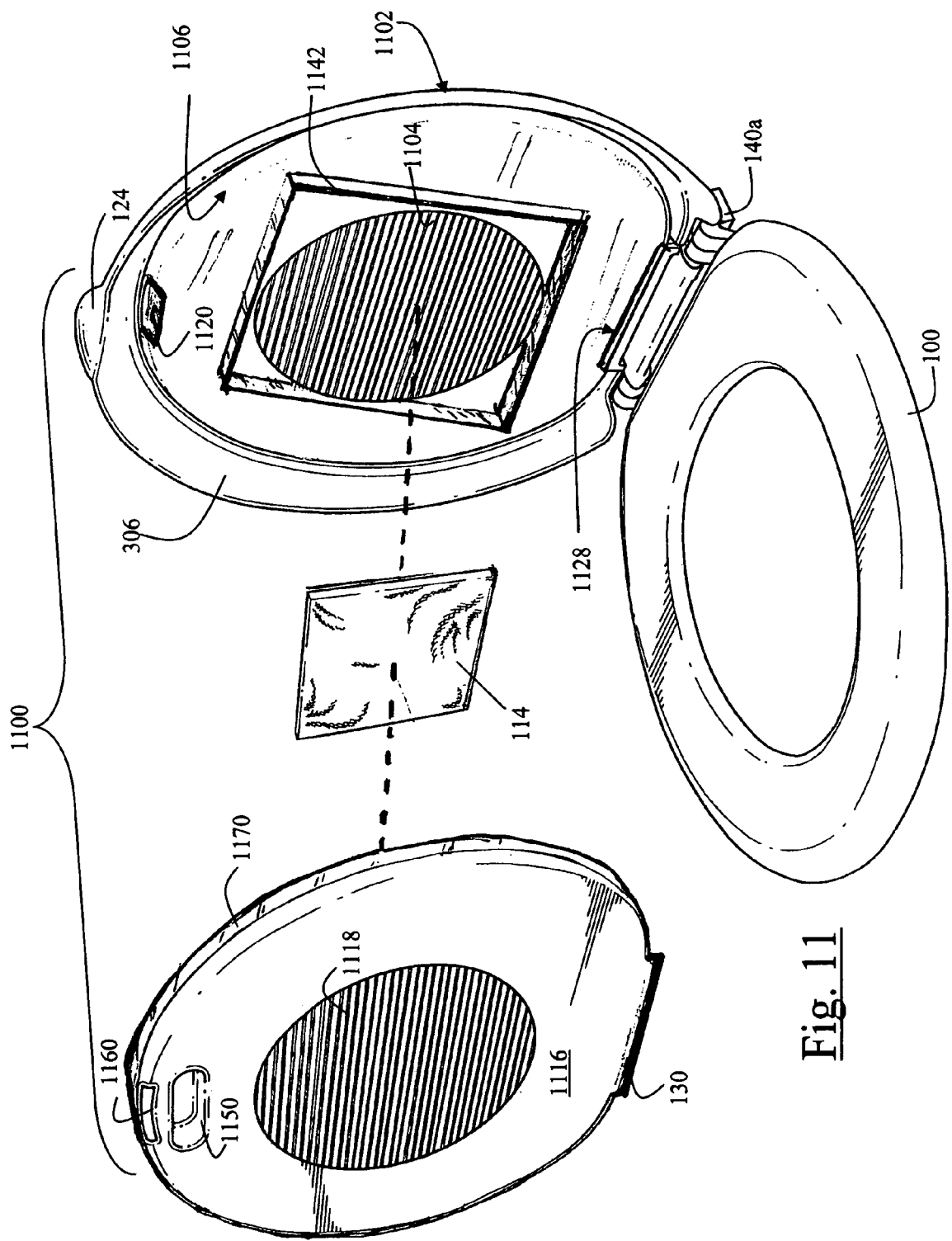
FIG. 11 is an alternative embodiment, illustrating an exemplary toilet seat and lid in accordance with the present invention.
Figure 12:
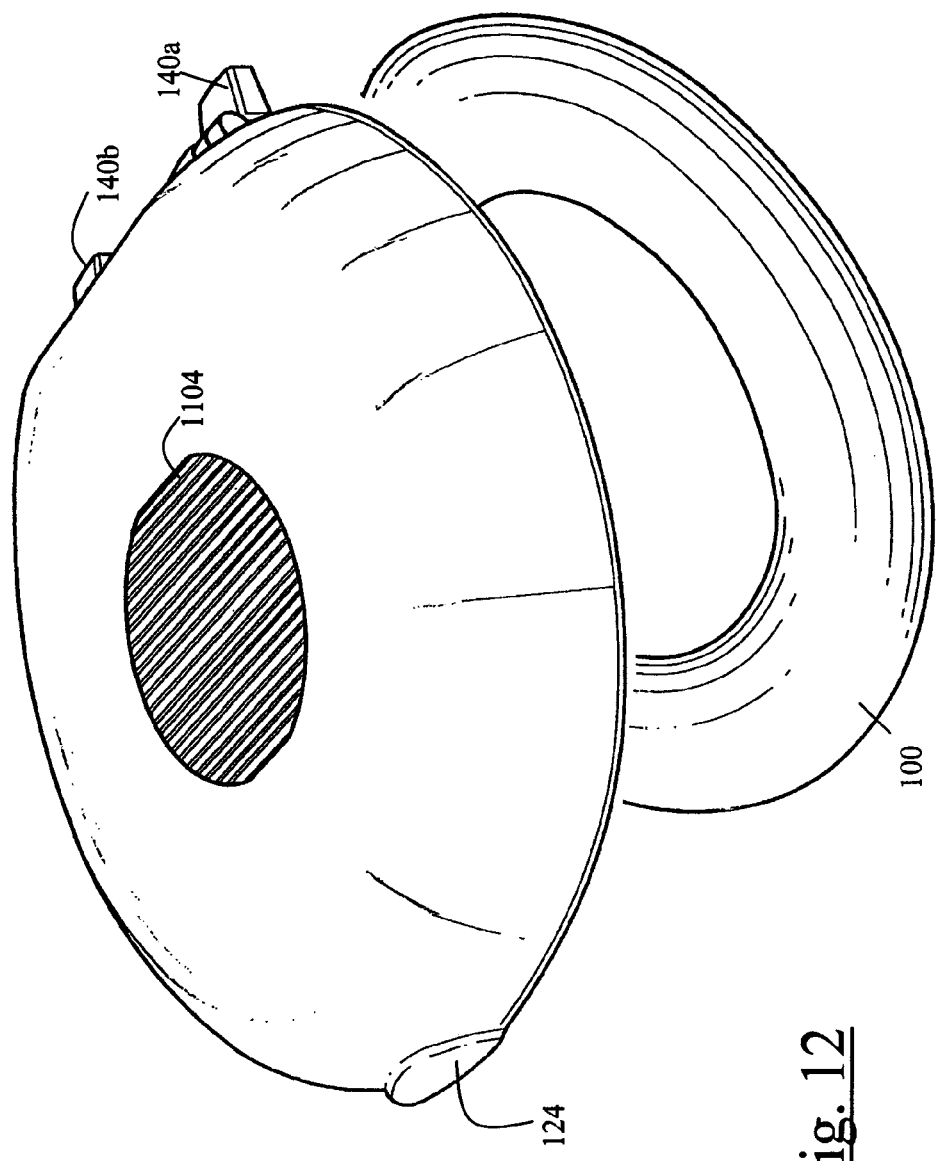
FIG. 12 is an exemplary perspective view, illustrating the assembled toilet seat and lid of FIG. 11 in accordance with the present invention.
Figure 13:
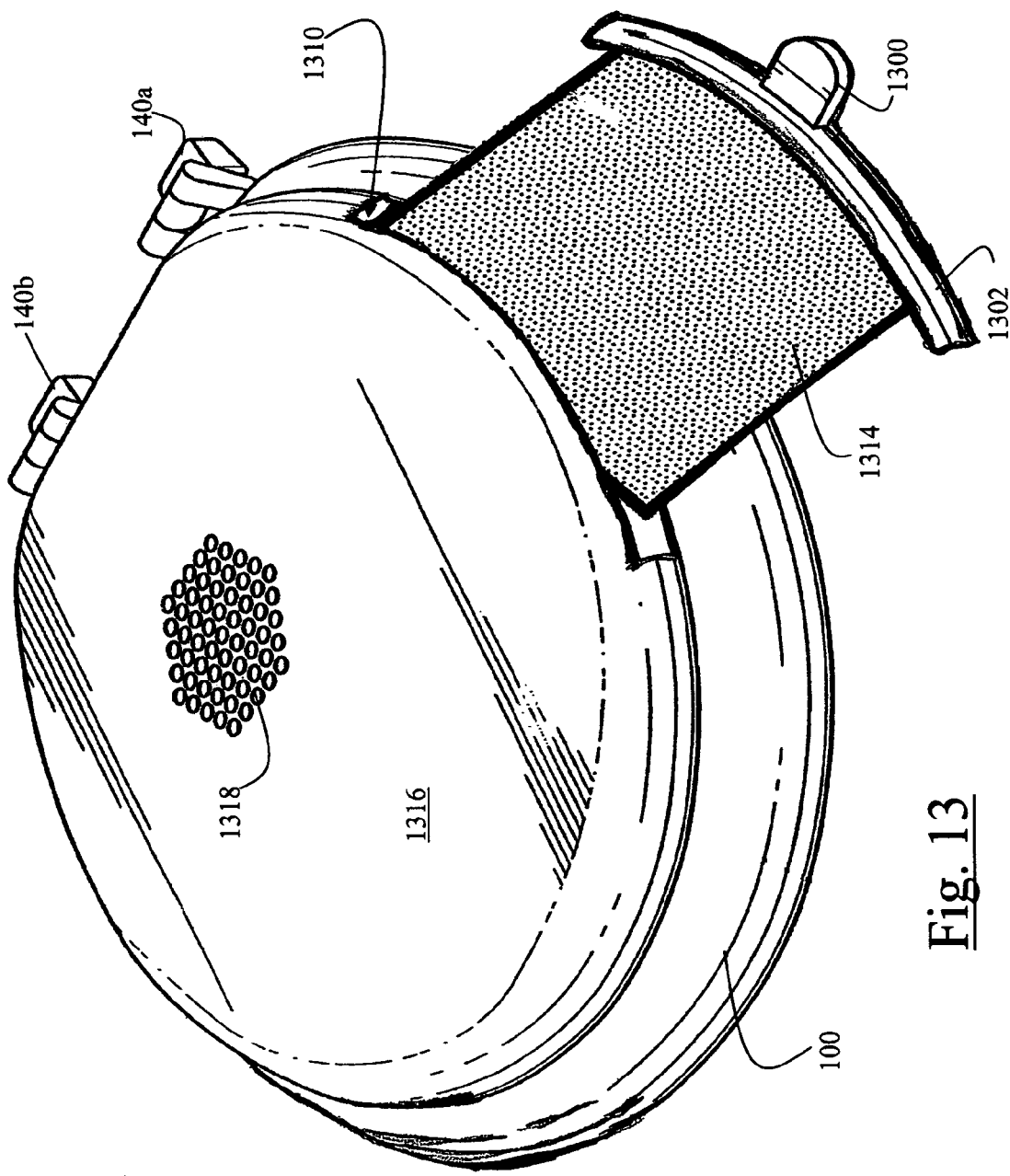
FIG. 13 is another alternative embodiment, illustrating an exemplary toilet seat and lid in accordance with the present invention.
Figure 14:
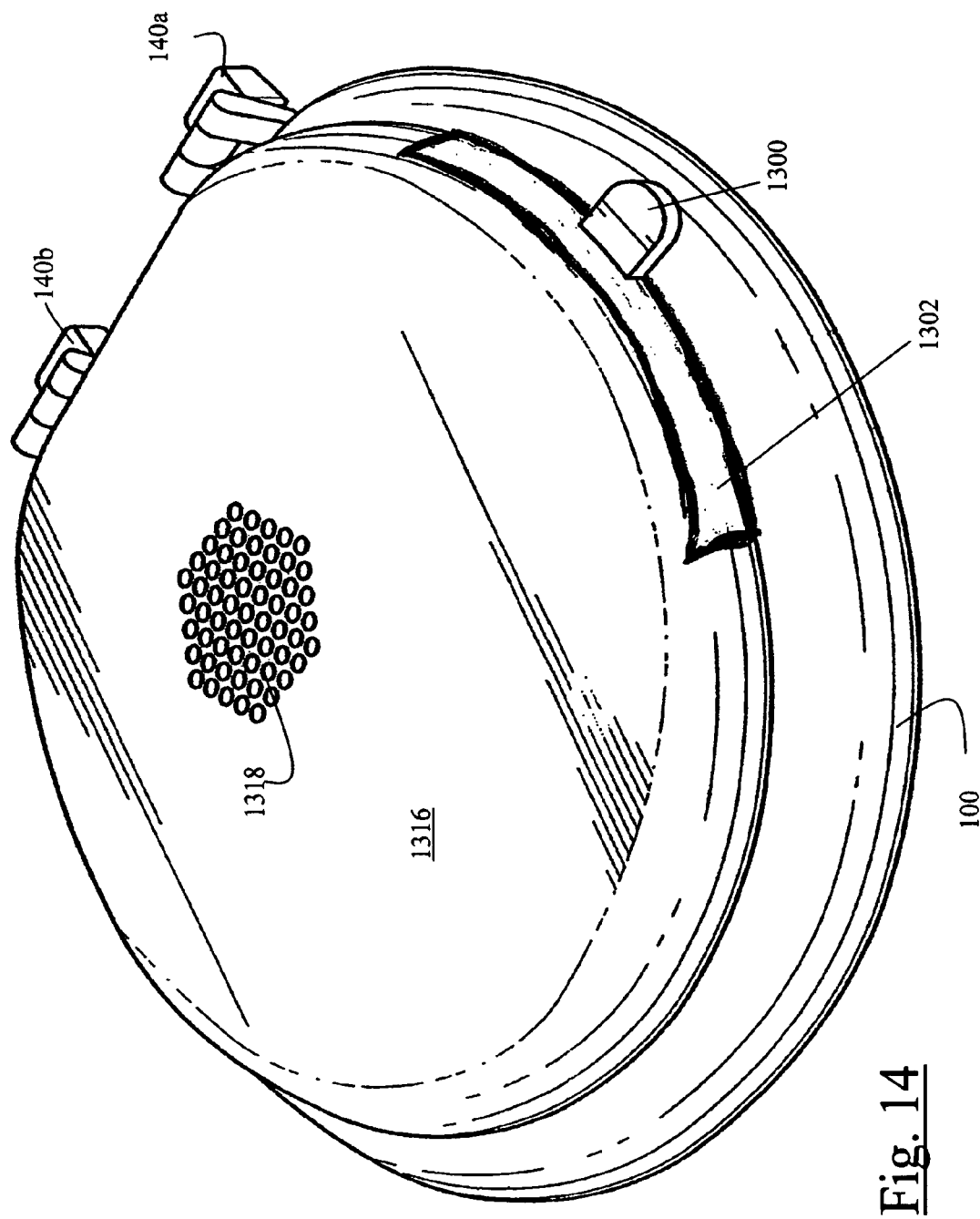
FIG. 14 is an exemplary illustration of the toilet seat and lid shown in FIG. 13, in a closed position in accordance with the present invention.
Figure 15:
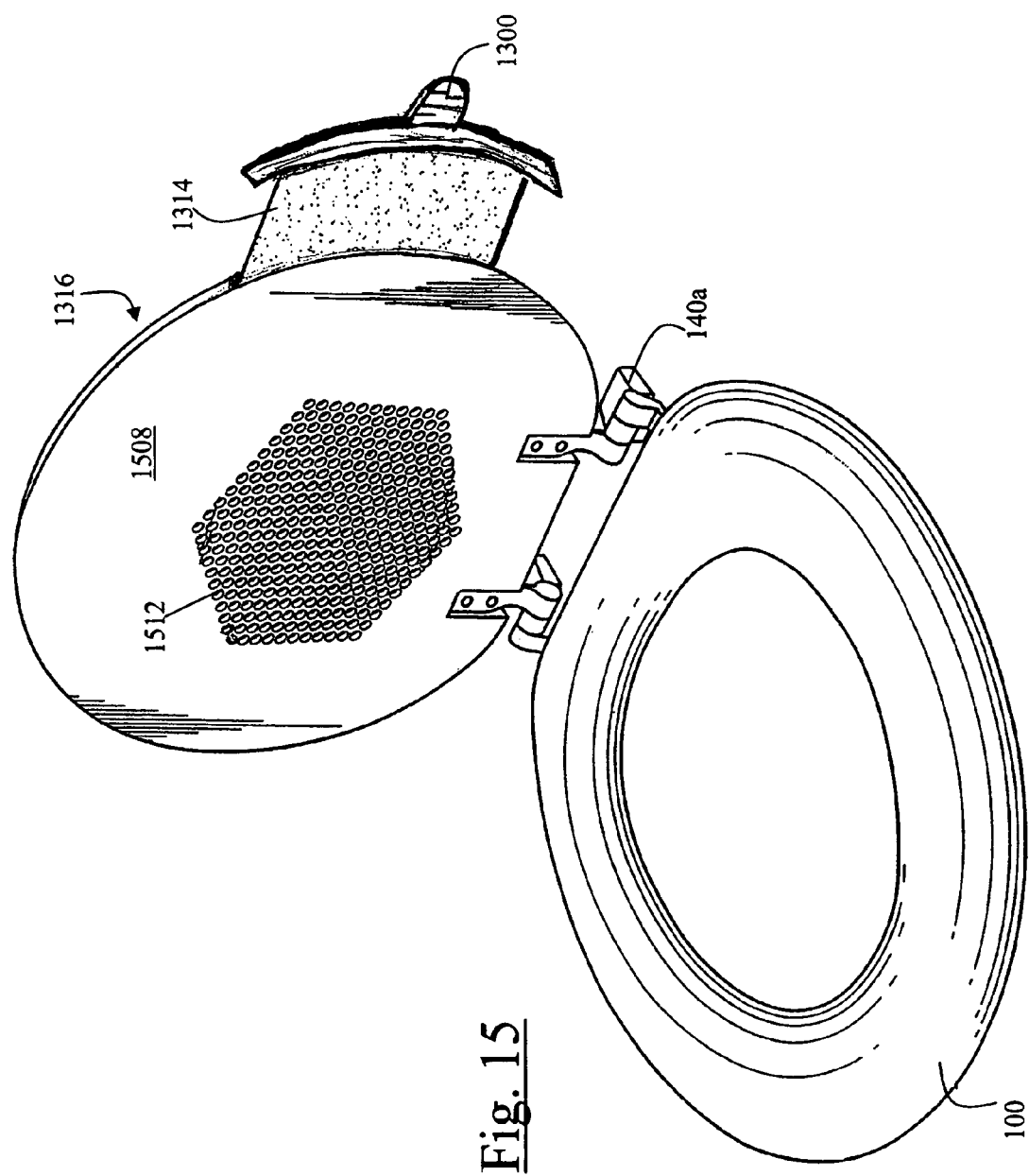
FIG. 15 is an exemplary illustration of the toilet seat and lid shown in FIG. 13, in an open position in accordance with the present invention.

FIG. 11 is an alternative embodiment, illustrating an exemplary toilet seat 100 and lid 1100 in accordance with the present invention in which the lid cap 1116 couples to the underside housing 1106 of the main lid section 1102, combining to form the lid 1100. As FIG. 11 illustrates, the main lid section 1102 of the lid 1100 includes the housing 1106, which is comprised of a vent or air holes 1104. The housing 1106 can be used to store any article 114 of appropriate size to detect, collect, contain, neutralize, and eliminate aerosolized contaminants 800 that ascend vertically out of the toilet bowl 700 as a result of flushing, without any moving parts, when the seat and the lid are in the closed position. The housing 1106 also includes structures 1142 for securing the article 114, and for providing structural integrity and strength for the lid 1100. The housing 1106 further includes an elongated recessed portion 1128 at a distal end near the two coupling hinges 140*a* and 140*b* for accommodating a protruded tab 130 located at the distal end of a lid cap 1116. The housing 1106 further includes a locking clip 1120 located at a proximal end of the housing 1106, projected outward from the underside of the main lid section 1102 of the lid 1100, and is received by an opening 1160 at a proximal end of the lid cap 1116. The protruded tab 130 is inserted within the elongated recess 1128 of the housing 1106, and the locking clip 1120 of the housing 1106 is snapped into the opening 1160 of the lid cap 1116 for securing the lid cap 1116 onto the main lid section 1102 for enclosing the housing 1106.

The housing 1106 is closed by the removable toilet lid cap 1116, which also includes a vent or air holes 1118 at a location commensurate with a location of the vent or air holes 1104 on the main lid section 1102. In general, it is preferred (optionally, only) if the size of the vent 1118 on the lid cap 1116 is made larger than the size of the vent 1104 on the main lid section 1102. However, the device of the present invention can function without size differences between the vents. In general, the size difference (smaller top vent and larger bottom vent) accelerates the venting process. That is, this difference may facilitate the acceleration of the vertical ascension of aerosols through the vent 1118, the housing 1106, pushing air out of the vent 1104. The circumference edge 1170 of the lid cap 1116 is fully inserted inside the main lid section 1102. A cavity 1150 at a proximal end near the opening 1160 is used for insertion of fingers for grasping the lid cap for facilitating the removal of the locking clip 1120 from the opening 1160. The underside of the lid cap 1116 (not shown) also includes support structure for added strength. The remaining components are identical to the embodiment illustrated in FIGS. 1-10. FIG. 12 illustrates the topside of the lid 1100, including the topside of the vent 1104.

FIG. 13 is another alternative embodiment, illustrating an exemplary toilet seat 100 and lid 1316 in accordance with the present invention. As illustrated, the lid 1316 is comprised of vent or air holes 1318, and includes housing 1310 for insertion of an article 1314 therein, the non-limiting examples of which may include one or any combination of sensors, analyzers, filters, collectors, sanitizers, etc. In this embodiment, the article 1314 further includes a tab handle 1300, and a coupler 1302, which connects the tab handle 1300 to the article 1314. FIG. 14 is an exemplary illustration of the toilet seat 100 and lid 1316 combination shown in FIG. 13, with the article 1314 fully inserted inside the housing 1310. FIG. 15 is an exemplary illustration of the same toilet seat 100 and lid 1316 combination shown in FIG. 13, but with the lid 1316 in an open position, and the article 1314 moved out of the housing 1310 to an extended position. As illustrated, the underside 1508 of lid 1316 is also comprised of vent or air holes 1512, with vent 1318 optionally configured smaller in size than the underside vent 1512.

FIGS. 16A to 16F are yet another alternative embodiment, illustrating an exemplary, preferred lid and toilet seat in accordance with the present invention. Referring to FIGS. 16A to 16F, the lid 1600 is comprised of a main lid section 1602 having a shroud 1618 that fully covers a gap between the lid 1600 and a seat 1626 by extending past a bottom edge 1631 of the toilet seat 1626. When the lid 1600 is in a fully closed position, the shroud 1618 blocks exiting of fecal and urinary aerosols during the act of flushing. The front end of the shroud 1618 includes a lid lift tab 1601 (FIG. 16B) that facilitates in raising and lowering the lid 1600 without touching the seat 1626. As illustrated, the lid lift tab 1601 is arched, and extends out, past the outer edge of the seat 1626 to allow a person to use a finger to lift or lower the lid 1600.

As further illustrated in FIGS. 16A to 16F, the main lid 1602 further includes an opening 1608 at a back end, and two connection mechanism 1610 and 1612 that couple the main lid 1602 with the back end of the toilet seat 1626 via a pair of respective pins, bars, or rod 1607*a* and 1607*b* through a set of apertures 1614 and 1616. As further illustrated, the lid 1600 further includes a single piece lid cap 1604 that couples with the underside of the main lid 1602, the coupled combination of which forms the lid 1600. The single piece lid cap 1604 includes a housing 1624, which is comprised of a first set of vent or air holes 1642. The housing 1624 can be used to store any article 114 of appropriate size to detect, collect, contain, neutralize, and eliminate aerosolized contaminants 800 that ascend out of the toilet bowl 700 as a result of flushing, without any moving parts, when the seat and the lid are in the closed position. The housing 1624 also includes structures 1620 and 1622 for securing the article 114, and for providing structural integrity and strength for the single piece lid cap 1604. The single piece lid cap 1604 further includes a second set of vent or air holes 1606 at a back end, which are aligned with the opening 1608 of the main lid 1602. That is, the outer perimeter of the structure of the vent or air holes 1606 on the back end of the single piece lid cap 1604 is inserted into the opening 1608 when the single piece lid cap 1604 is coupled with the main lid 1602. Accordingly, with this preferred embodiment, both sets of vents 1642 and 1606 are on the same piece, which is the single piece lid cap 1604. This is preferred because the top surface of the main lid 1602 remains smooth with no vents. The benefit of having a smooth exterior top surface and with no vents on the main lid 1602 is that it provides a true "conventional" look and feel of a typical conventional toilet lid, improving marketability. In addition, the main lid 1602 with no vents enables for easier cleaning and maintenance. In other words, the main lid 1602, which is attached to the toilet bowl 700 by the coupling hinges 140*a* and 140*b*, has no vents to clean, and can be easily cleaned in a conventional manner. With the present embodiment, all vents 1642 and 1606 are on a single, detachable lid cap piece 1604 that is easily removed for cleaning. The single piece lid cap 1604 can be detached from the main lid 1602 and placed under running water or soaked in other cleaning agents, cleaned, and re-coupled with the main lid 1602 after cleaning.

As further illustrated, the seat 1626 is comprised of a seal 1632 that is connected to the underside 1660 of the seat 1626 to enclose the gap between the toilet seat 1626 and a top surface opening of the toilet bowl 700 (FIG. 16C). This closing of the gap prevents the exiting of any possible horizontally moving toxins, fecal, or other contaminant aerosols due to flushing when the lid and seat are in the closed position. The seal 1632 may be installed in a variety of methods, including those illustrated in the previous figures or by a simple adhesive such as glue. As one specific, non-limiting example, the seal 1632 may include a continuous protrusion 1605 raised from the flat section 1603, which may fit securely into a corresponding or complementary groove or a recess (not shown) within the underside 1660 of the toilet seat 1626, using an exemplary tongue and groove coupling technique. Alternatively, the groove or recess may instead be within the seal 1632, whereas the underside 1660 of the toilet seat may include a continuous protrusion, which may fit within the seal recess. As best illustrated in FIG. 16D, the seal 1632 is continuously placed around the underside 1660 of the toilet seat 1626. As further illustrated in FIGS. 16A to 16D, the toilet seat 1626 and lid 1600 combination of the present invention also includes an optional seat lift tab 1654 that facilitates in raising and lowering of the toilet seat 1626.

As illustrated in FIG. 16B, the article 114 is housed within the housing 1624 of the lid cap 1604. One of the sides of the article 114 is slipped under a retainer lip 1650, and the opposite side thereof is held in placed by a set of protrusions 1648 on an underside 1644 of the main lid section 1602 when the main lid section 1602 and the single piece lid cap 1604 are coupled with one another. This arrangement secures the article 114 on top of the vent 1642 within the housing 1624. As further illustrated, the underside 1644 of the main lid 1602 is also comprised of structures 1620 and 1670 for providing structural integrity and strength for the main lid section 1602. The perimeter wall structure 1670 on the main lid 1602 encompasses an area 1646, with the wall structure 1670 directly resting on the perimeter wall structure 1622 that encompasses and forms the housing 1624, further securing the article 114. Further, the height of the wall structure 1670 varies from the front to the back end, with the back end 1611 slanted towards the surface of the underside 1644 of the main lid 1602. The variation in the height of the wall structure 1670 is inversely proportional with the variation in the height of the perimeter wall structure 1622. That is, the slanted back end 1611 rests on the raised wall structure 1613 of the single piece lid cap 1604. When joined, this allows for a naturally rising conduit structure for airflow that exists at the back vent 1606, best illustrated in FIG. 16C. As further illustrated, the underside 1644 of the main lid 1602 is also comprised of a recessed perimeter 1617 that accommodates and houses a raised edge 1615 along the outer perimeter of the single piece lid cap 1604, further securing and improving sealing to thereby better guide the airflow through the vent 1642 and out the back vent 1606. The above described improvements for the housing 1624 for storing the article 114 enables easier maintenance and replacement of the article 114. When removing the single piece lid cap 1604 for cleaning, the housing 1642 and, in particular, the retainer lip 1650 secure and hold the article 114 in place. That is, the housing 1624 and the retainer lip 1650 prevent the article 114 from accidentally falling into the toilet bowl 700 when the single piece lid cap 1604 is removed or detached for cleaning.

As further illustrated, the underside 1644 of the main lid 1602 further includes a locking pocket 1603 that is protruded outward from the underside 1644 of the main lid 1602 of the lid 1600, which receives a locking clip 1652 on the lid cap 1604. The locking clip 1652 includes a locking lip 1652a, which is inserted and interlocked within the locking pocket 1603 when the lid cap 1604 is closed. The protuberance 1640 creates a cavity 1664 at an underside 1662 (FIGS. 16D and 16E) of the lid cap 1604 and is used for insertion of fingers for grasping the lid cap 1604 for facilitating the removal of the locking clip 1652 from the locking pocket 1603.

Figure 16A:
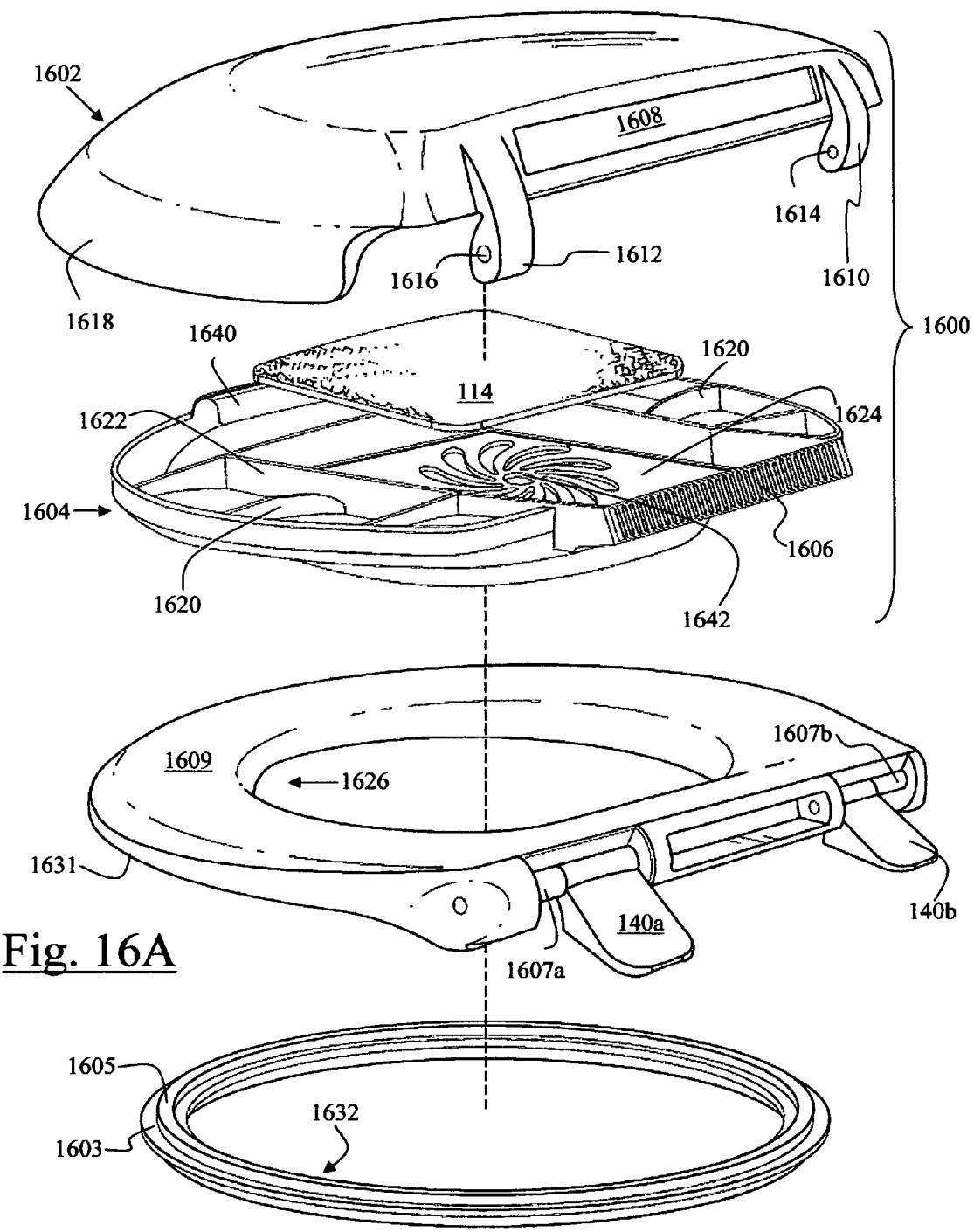
FIG. 16A is an exemplary illustration of yet another embodiment of a toilet seat and lid in accordance with the present invention.
Figure 16B:
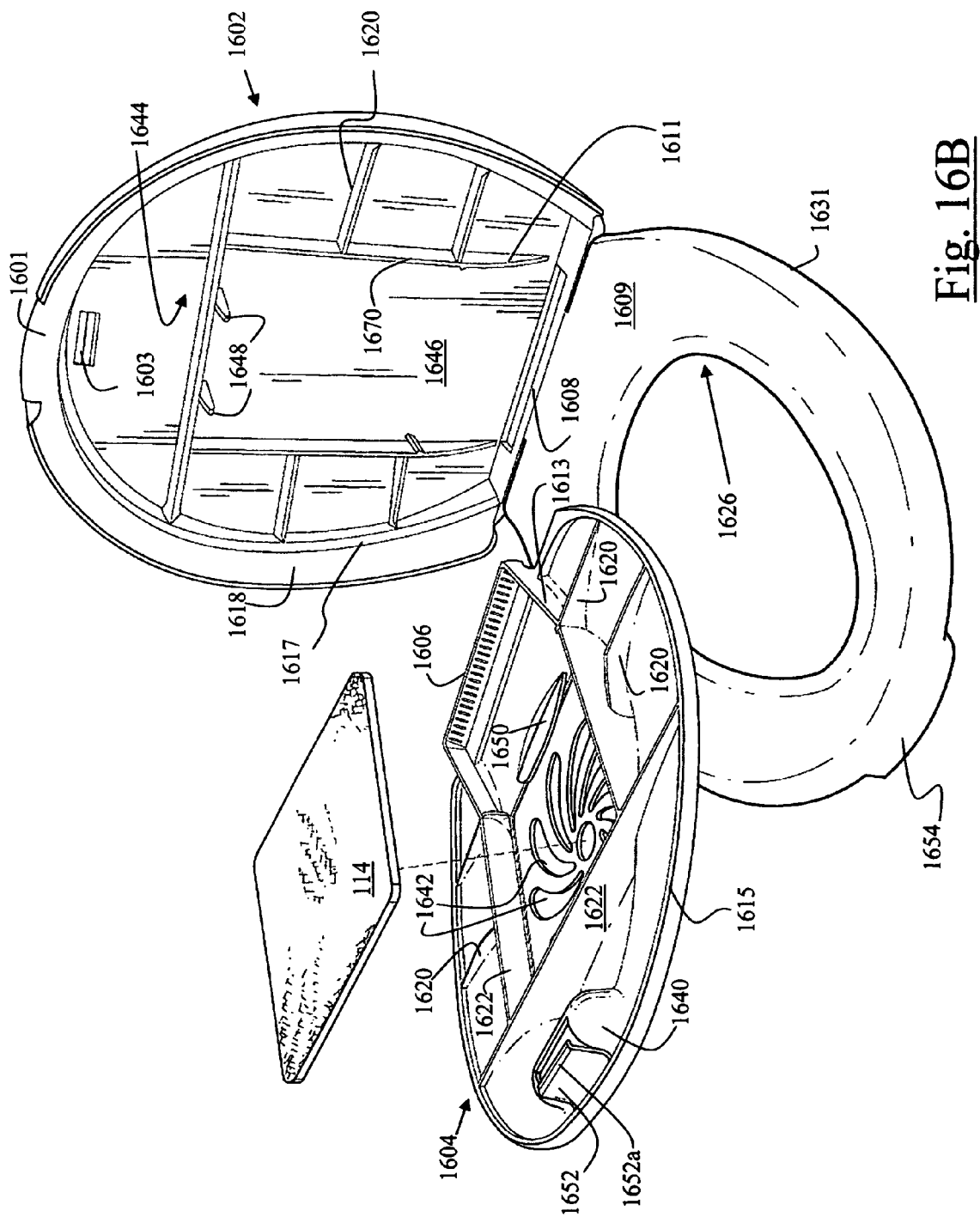
FIG. 16B is an exemplary exploded front perspective view of the toilet seat and lid illustrated in FIG. 16A.
Figure 16C:
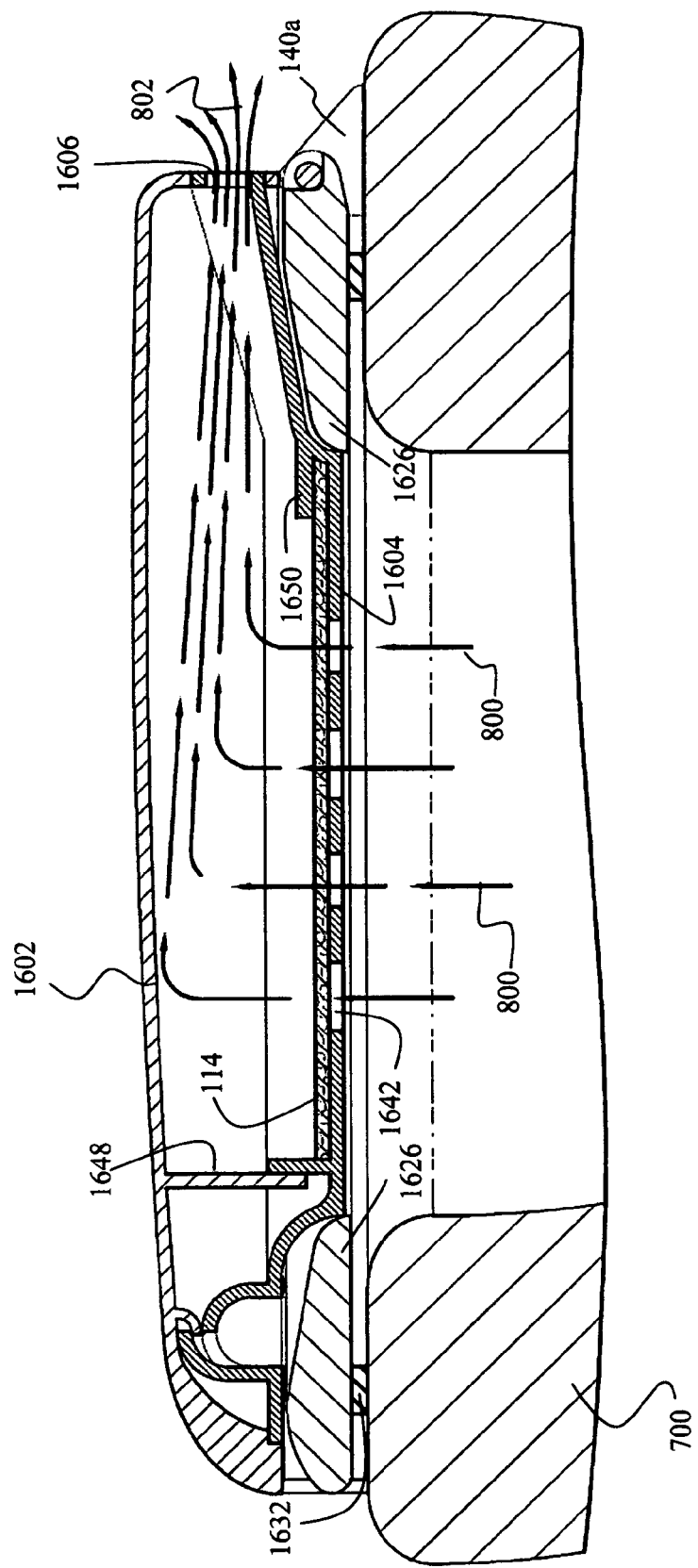
FIG. 16C is an exemplary cross-sectional view of the toilet seat and lid illustrated in FIG. 16A.
Figure 16D:
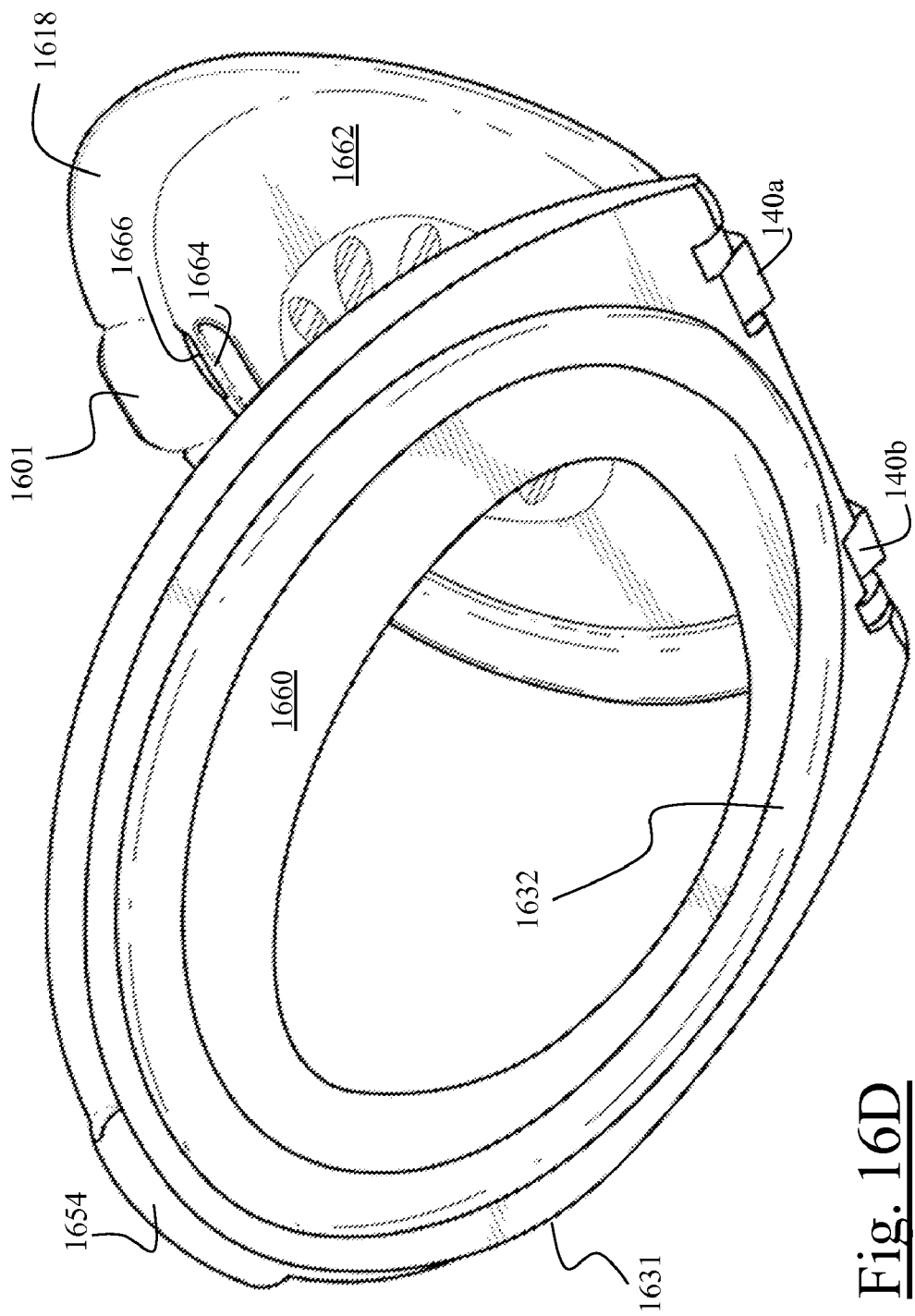
FIG. 16D is an exemplary bottom perspective view of the toilet seat and lid illustrated in FIG. 16A.
Figure 16E:
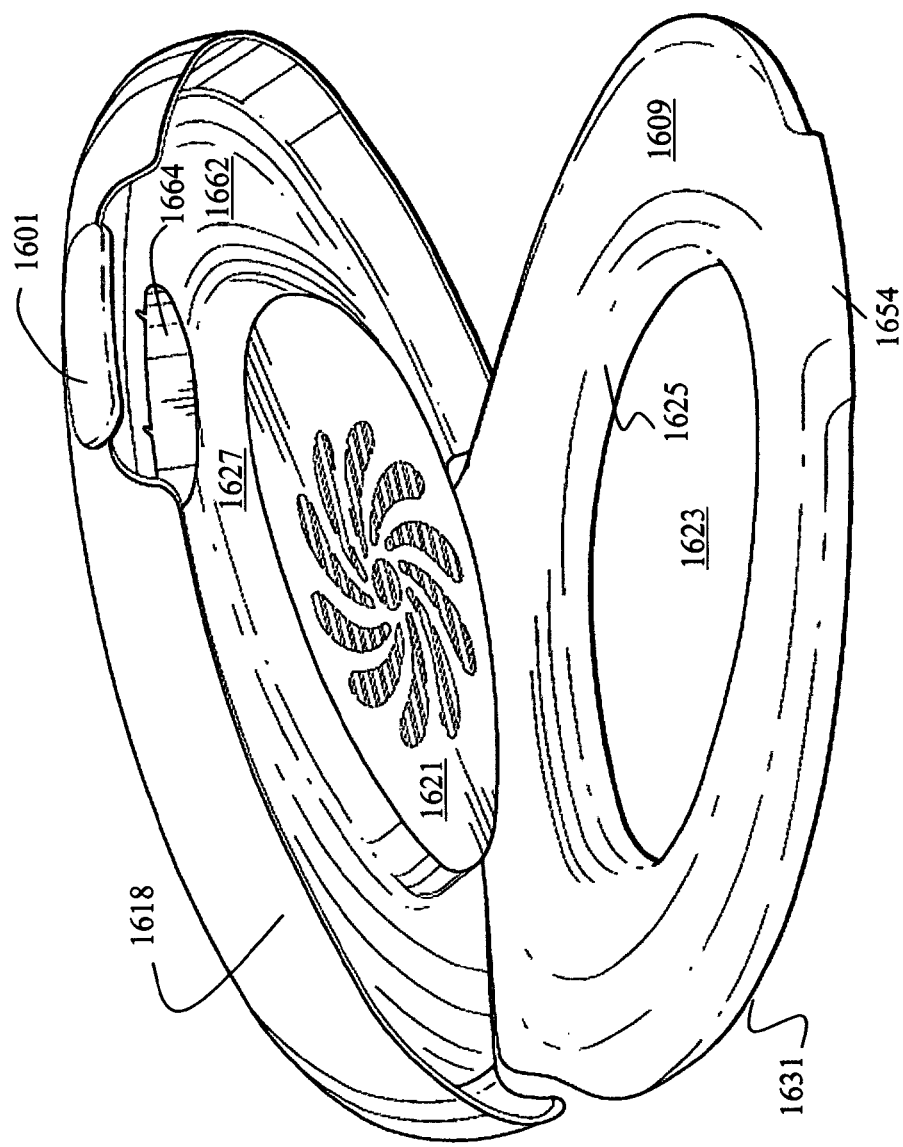
FIG. 16E is an exemplary assembled front perspective view of the toilet seat and lid illustrated in FIG. 16A.
Figure 16F:
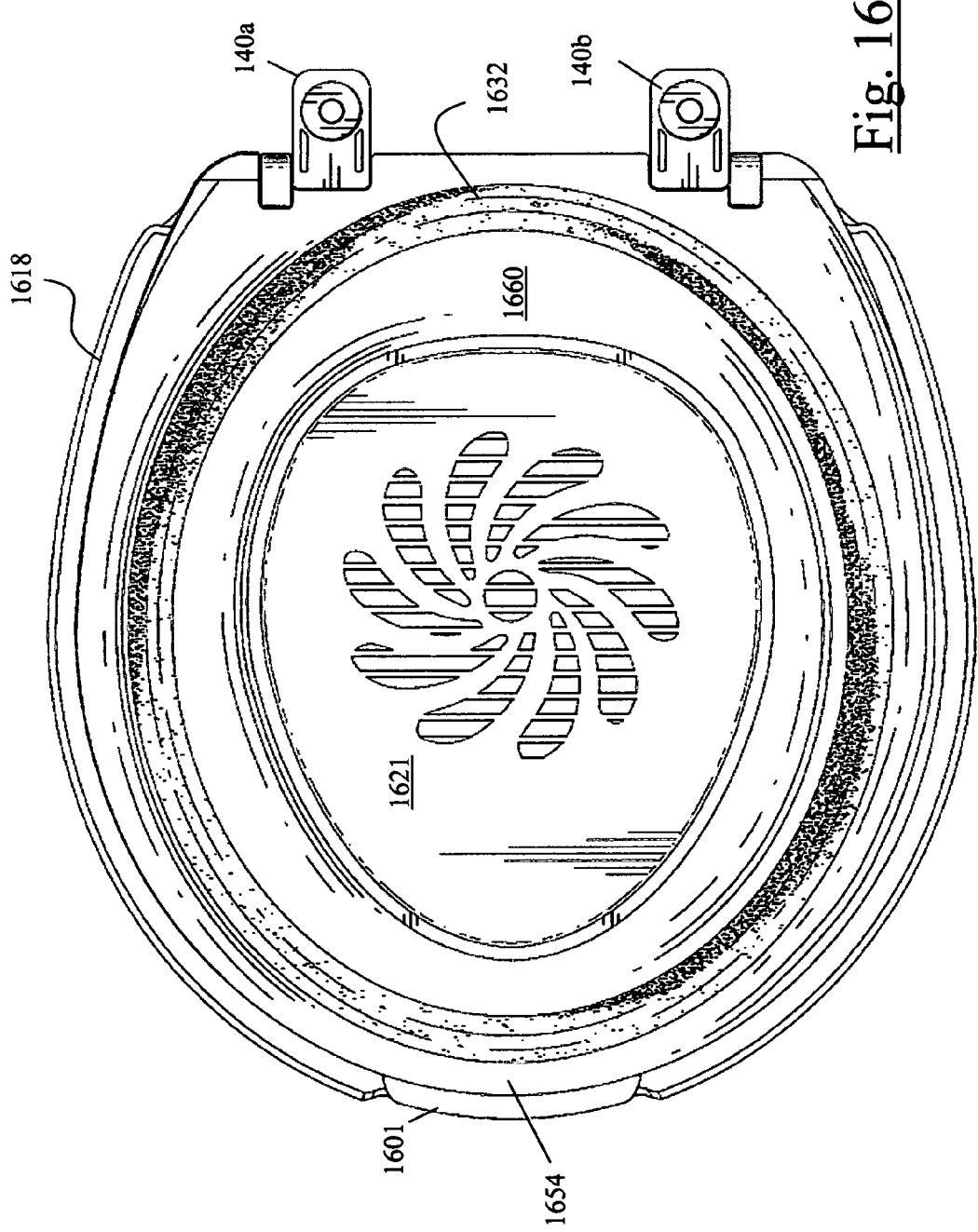
FIG. 16F is an exemplary bottom perspective view of the toilet seat and lid illustrated in FIG. 16A, but in closed position.

As best illustrated in FIGS. 16D, 16E, and 16F, the underside 1662 of the single piece lid cap 1604 is contoured to rest and be commensurately congruent with the top surface 1609 of the toilet seat 1626, forming a tight, snug fit seal. As illustrated, the underside 1662 includes a substantially protruded oval section 1621, which, when in closed position in relation to the toilet seat, is moved into a corresponding, substantially oval shaped toilet seat opening 1623. The oval section 1621 has an elevation 1627 that is inversely contoured to complement the inner edge periphery 1625 of the toilet seat, forming a tight seal.

FIG. 16C illustrates a cross-sectional view, showing a fully assembled and connected toilet bowl 700, seat 1626, and lid 1600, illustrating the flushing action, including the flow dynamics of aerosolized contaminants 800 in accordance with this embodiment of the present invention. The shroud 1618 is not illustrated for clarity. When the seat 1626 and the lid 1600 are in the closed position, during the first part of the flush cycle, a vertically ascending toxic, bacterial, and viral aerosol (spray) 800 is created (the "sneeze effect") when the toilet water 704 is pushed in the bowl 700. The aerosol or other contaminants (toxins, bacteria, viruses, etc.) 800 is mostly spewed vertically, and is forced to exit through the vent or air holes 1642 and the housing 1624, but only uncontaminated air 802 is exited through the back vent or air holes 1606. Upon coming into contact with the article 114 within the housing 1624 (which may contain any combination of sensors, analyzers, container dishes, filter-sanitizers, etc.), most of the contaminants or bacteria and viruses are detected, collected, contained and or killed by the article 114, allowing uncontaminated air 802 to exit from the vent 1606. During second part of every flush cycle, a suction is created within the bowl 700 when the toilet water 704 leaves the bowl 700 through the drainpipe 702, pulling the air into the bowl 700 through the vent or air holes 1606, the housing 1624, and the vent or air holes 1642. Accordingly, the present invention prevents droplets or airborne toxins, contaminants, or other bacterial or viral aerosols 800 to plume and permeate out of the toilet bowl 700 when the seat 1626 and lid 1600 combination of the present invention are in the closed position.

More particularly, the present invention closes a first gap or opening between the toilet lid 1600 and the toilet seat 1626 to contain and block exiting aerosolized contaminants 800 during a flush. The present invention further closes a second gap or opening between the toilet seat 1626 and the top surface opening of the toilet bowl 700 when the toilet seat 1626 is in the closed position to contain and block exiting aerosolized contaminants during the flush. Enclosing the first and second openings create a single means of escape for air within the toilet bowl, which is only through the disclosed vents 1642 and 1606. Another purposes for closing the first and the second opening is to generate an air pressure within the toilet bowl when the water is pushed into the commode 700 during the flush to effect a siphon. The pressurized air, due to delivered water into the toilet bowl pushes any aerosolized contaminant out of the bowl through the disclosed vents during the flush cycle without using electrical, UV systems, or any moving parts such as fans, motors, vacuum tubes, and only through the natural, well-known function of a flush.

More technically, the toilet lid 1600 and the toilet seat 1626 in closed positions, close the first and the second gaps or openings. During a first phase of a flush cycle, water 704 is delivered into the toilet bowl 700 to effect a siphon. The delivered water 704 displaces and compresses air within the toilet bowl. This generates an increasing air pressure therein the bowl (due in part to the sealing or blocking of first and second gaps) that is pushed upward and laterally as a volume of delivered water continues to increase and fill the toilet bowl 700 to effect a siphon. With the increased volume of water pushing the pressurized air, the aerosolized contaminants within the toilet bowl 700 have no other escape but to move vertically up to ascend and exit the toilet bowl through the only openings, which are the disclosed vents 1642 and 1606, while the closed first and the second gaps block exiting of the aerosolized contaminants. That is, the pressurized air (moving upward or laterally) takes the path of least resistance, pushing along with it the aerosolized contaminants within the toilet bowl 700 vertically up to ascend and to exit the toilet bowl 700 through the vents 1642 and 1606 without using electrical, UV systems, or any moving parts such as fans, motors, vacuum tubes, and only through the natural, well-known function of a flush, while the closed first and the second gaps block exiting of the aerosolized contaminants. The pressurized air between the vents 1642 and 1606 having passed through the article 114 moves into the conduit structure, where it is naturally guided to exit at the back vent 1606.

During a second phase of the flush cycle, water 704 leaves the toilet bowl 700 as a result of the siphon and a natural gravitational pull, generating a suction that pulls in air into the toilet bowl 700 through vents, while the closed first and the second gaps block movement of air through the first and the second gaps. During a third (final) phase of the flush cycle, the toilet bowl is refilled with water 704, which displaces and compresses air within the toilet bowl 700. This generates an increasing air pressure therein that is pushed upward as the delivered water 704 continues to fill the toilet bowl 700. The delivered water pushes the pressurized air and remaining aerosolized contaminants within the toilet bowl 700 vertically up to ascend and exit the toilet bowl through the vents (or openings), while the closed first and the second gaps block exiting of any remaining aerosolized contaminants.

Although the invention has been described in considerable detail in language specific to structural features and or methodological steps, it is to be understood that the invention defined in the appended claims is not necessarily limited to the specific features or steps described. Rather, the specific features and steps are disclosed as preferred forms of implementing the claimed invention. Therefore, while illustrative embodiments of the invention have been described, numerous variations and alternative embodiments will occur to those skilled in the art. For example, the protruded tab of the lid cap and the elongated recess on the main lid section for any of the embodiments may be replaced by a hinge mechanism to allow the opening and closing of the lid cap in relation to the main lid section in the same manner as the lid is opened and closed in relation to the seat. This would allow the lid cap to open and close from the top, and pivot on the hinge at the bottom, which connects to the main lid section. Another alternative would be to place the same hinge mechanism at the proximal end (the top of the main lid section and the lid cap) to replace the locking clip and aperture combination instead, and provide well-known locking schemes at a distal end, replacing the protruded tab of the lid cap and the elongated recess on the main lid section. This would allow the lid cap to open and close from the bottom, and pivot on the hinge at the top, which connects to the main lid section. Such variations and alternate embodiments are contemplated, and can be made without departing from the spirit and scope of the invention.

It should further be noted that throughout the entire disclosure, the labels such as left, right, front, back, top, bottom, forward, reverse, clockwise, counter clockwise, up, down, or other similar terms such as upper, lower, aft, fore, vertical, horizontal, proximal, distal, parallel, perpendicular, etc. have been used for convenience purposes only and are not intended to imply any particular fixed direction or orientation. Instead, they are used to reflect relative locations and/or directions/orientations between various portions of an object.

In addition, reference to "first," "second," "third," and etc. members throughout the disclosure (and in particular, claims) is not used to show a serial or numerical limitation but instead is used to distinguish or identify the various members of the group.

In addition, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of," "act of," "operation of," or "operational act of" in the claims herein is not intended to invoke the provisions of 35 U.S.C. 112, Paragraph 6.

What is claimed is:

1. A device for containment and elimination of aerosolized contaminants, comprising:
   a toilet lid coupled with a toil seat, and when in a closed position, a first gap between the toilet lid and the toilet seat is fully enclosed to contain and block exiting aerosolized contaminants through the first gap during a flush;
   the toilet seat is comprised of a continuous seal coupled with an underside of the toilet seat to fully enclose a second gap between the toilet seat and a top surface opening of a toilet bowl when the toilet seat is in the closed position to contain and block exiting aerosolized contaminants through the second gap during the flush;
   the toilet lid including a main lid section and a single piece lid cap that is detachably coupled with the main lid section;
   the single piece lid cap includes a placement for accommodating an article, and further includes a first vent and a second vent, with the article positioned within the placement, in between the first and the second vents;
   the placement includes a retainer lip to securely, and removably retain the article on top of the first vent;
   with the toilet lid and the toilet seat in closed positions to close the first and the second gaps, when water is delivered into the toilet bowl, the delivered water displaces and compresses air within the toilet bowl, generating an increasing air pressure therein that is pushed upward as a volume of delivered water continues to increase and fill the toilet bowl, with the increased volume of water pushing the pressurized air and the aerosolized contaminants within the toilet bowl vertically up to ascend and exit the toilet bowl through the first vent, the article, and then the second vent at the back end of the single piece lid cap, while the closed first and the second gaps block exiting of the aerosolized contaminants;
   the first vent is located normal to the vertical upward move of the aerosolized contaminants, and the second vent is located at a back end of the single piece lid cap, oriented substantially parallel to the vertical upward move of the aerosolized contaminants;
   with the aerosolized contaminants detected, collected, contained, neutralized, and eliminated by the article, allowing only uncontaminated air out of the first and second vents, and only through the natural upward movement of the aerosolized contaminants due to the flush cycle, without using electrical or moving components.

2. The device as set forth in claim 1, wherein:
   the main lid section further including a top surface that is smooth; and
   a shroud section that fully covers and extends past a bottom edge of the toilet bowl for covering gaps between the lid and the toilet bowl for containment of exiting aerosolized contaminants.

3. The device as set forth in claim 1, wherein:
   an underside of the single piece lid cap is contoured to rest and be commensurately congruent with a top surface of the toilet seat, forming a tight, snug fit seal; and
   the underside of the single piece lid cap further includes a substantially protruded section, which, when in closed position in relation to the toilet seat, is moved into a correspondingly configured toilet seat opening, with the protruded section having an elevation that is inversely contoured to complement an inner edge periphery of the toilet seat, further facilitating a tight seal between the toilet lid and the toilet seat.

* * * * *